US012370688B2

(12) United States Patent
Gomez et al.

(10) Patent No.: US 12,370,688 B2
(45) Date of Patent: Jul. 29, 2025

(54) SYSTEMS AND METHODS FOR DETERMINING REGISTRATION OF ROBOTIC MANIPULATORS OR ASSOCIATED TOOLS AND CONTROL

(71) Applicant: INTUITIVE SURGICAL OPERATIONS, INC., Sunnyvale, CA (US)

(72) Inventors: Daniel H. Gomez, Los Gatos, CA (US); Arsen Babayan, San Jose, CA (US); Raul Herrera Barcenas, Newark, CA (US); Marc E. Tognaccini, Morgan Hill, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 376 days.

(21) Appl. No.: 17/913,665

(22) PCT Filed: Mar. 24, 2021

(86) PCT No.: PCT/US2021/023799
§ 371 (c)(1),
(2) Date: Sep. 22, 2022

(87) PCT Pub. No.: WO2021/195158
PCT Pub. Date: Sep. 30, 2021

(65) Prior Publication Data
US 2023/0116795 A1    Apr. 13, 2023

Related U.S. Application Data

(60) Provisional application No. 62/993,960, filed on Mar. 24, 2020.

(51) Int. Cl.
*B25J 9/16* (2006.01)
*A61B 34/35* (2016.01)
(Continued)

(52) U.S. Cl.
CPC ............. *B25J 9/1682* (2013.01); *A61B 34/35* (2016.02); *A61B 34/37* (2016.02); *B25J 9/0084* (2013.01);
(Continued)

(58) Field of Classification Search
CPC ...... B25J 9/1682; B25J 9/1689; B25J 9/1692; A61B 34/35; A61B 34/70; A61B 90/06;
(Continued)

(56) References Cited

U.S. PATENT DOCUMENTS

| 6,788,018 B1 | 9/2004 | Blumenkranz |
| 2013/0123981 A1* | 5/2013 | Lee ...................... H04W 4/024 901/1 |

(Continued)

FOREIGN PATENT DOCUMENTS

| JP | H1083208 A | * | 3/1998 |
| KR | 20190120108 A | * | 10/2019 |

(Continued)

OTHER PUBLICATIONS

Seok et al., KR 20190120108 A, "Autonomous Working System, Method, and Computer Readable Recording Medium", Pub: Oct. 23, 2019, English Translation (Year: 2019).*

(Continued)

*Primary Examiner* — Jason Holloway
*Assistant Examiner* — Benjamin J Brosh
(74) *Attorney, Agent, or Firm* — Haynes & Boone, LLP.

(57) ABSTRACT

A robotic system includes first and second manipulator assemblies in an operating environment and having separately movable bases. A processing unit is configured to receive first sensor data from a first plurality of sensors disposed on the first manipulator assembly, wherein the first sensor data provide spatial information about the operating environment external to the first manipulator assembly. A (Continued)

first spatial relationship of the second manipulator assembly relative to the first manipulator assembly is determined using data including the first sensor data. A first alignment relationship between the first and second manipulator assemblies is established based on the first spatial relationship. Based on the first alignment relationship, motion of the second manipulator assembly is commanded in response to a command from a first input device operable by an operator.

26 Claims, 11 Drawing Sheets

(51) Int. Cl.
*A61B 34/37* (2016.01)
*B25J 9/00* (2006.01)
*A61B 34/20* (2016.01)

(52) U.S. Cl.
CPC ........... *B25J 9/1689* (2013.01); *B25J 9/1692* (2013.01); *A61B 2034/2055* (2016.02); *G05B 2219/40605* (2013.01)

(58) Field of Classification Search
CPC ......... A61B 90/92; A61B 90/94; A61B 90/98; A61B 2034/2055; A61B 2034/2059; A61B 2034/2063; A61B 2034/302; G05B 2219/40584; G05B 2219/40605
See application file for complete search history.

(56) References Cited

U.S. PATENT DOCUMENTS

| | | | |
|---|---|---|---|
| 2016/0023355 A1* | 1/2016 | Komatsu | B25J 9/1682 901/8 |
| 2016/0184032 A1* | 6/2016 | Romo | B25J 13/085 901/46 |
| 2020/0094411 A1* | 3/2020 | Tan | B25J 9/1661 |
| 2020/0367977 A1* | 11/2020 | Liu | A61B 34/30 |
| 2021/0263533 A1* | 8/2021 | Motoyama | G06V 20/58 |

FOREIGN PATENT DOCUMENTS

| | | |
|---|---|---|
| WO | WO-2019099346 A2 | 5/2019 |
| WO | WO-2019103954 A1 | 5/2019 |

OTHER PUBLICATIONS

Nogo et al., JP H1083208 A, "Arithmetic Mechanism for Inter-Robot Relative Position", Pub: Mar. 31, 1998, English Translation (Year: 1998).*
International Preliminary Report on Patentability for Application No. PCT/US2021/023799, mailed Oct. 6, 2022, 10 pages.
International Search Report and Written Opinion for Application No. PCT/US2021/023799, mailed Jul. 7, 2021, 16 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

SYSTEMS AND METHODS FOR DETERMINING REGISTRATION OF ROBOTIC MANIPULATORS OR ASSOCIATED TOOLS AND CONTROL

CROSS-REFERENCE TO RELATED APPLICATIONS

This application is the U.S. National Stage patent application of International Patent Application No. PCT/US2021/023799 filed on Mar. 24, 2021 which claims the benefit of U.S. Provisional Application 62/993,960 filed Mar. 24, 2020, each of which is incorporated by reference herein in its entirety.

FIELD

The present disclosure is directed to systems and methods for performing a robotic procedure, and more particularly to systems and methods for determining registration of robotic manipulators for controlling the movement of the robotic manipulators and/or associated tools.

BACKGROUND

Robotic manipulator assemblies include one or more robotic manipulators that can be operated to control the motion of tools in a workspace. For example, such robotic manipulators can be used to perform non-medical and medical procedures. As a specific example, teleoperated surgical manipulators can be used to perform minimally invasive medical techniques.

It is desirable in medical techniques to improve patient outcomes and facilitate clinician procedures for diagnosis or treatment. For example, for medical procedures involving entry into a patient anatomy, minimally invasive techniques may be performed through natural orifices in the patient anatomy or through one or more incisions. Through these natural orifices or incisions, clinicians may insert medical tools to reach a target tissue location. Minimally invasive medical tools include tools such as therapeutic tools, diagnostic tools, and surgical tools. Minimally invasive medical tools may also include imaging tools such as endoscopic tools that provide a user with a field of view within the patient anatomy. Robotic medical systems allow a user to control medical instruments via a manipulator. The manipulator may include two or more links coupled together by one or more joints. The joints may include actively controlled joints whose position or motion is actively driven by actuators. The joints may also include passive joints, whose position or motion is not actively driven by actuators.

Robotic manipulators may be teleoperated or otherwise computer-assisted. For performing and viewing a robotic procedure at a procedure site (e.g., a surgical site within a patient), two or more manipulators may be used for holding and manipulating tools, including for example surgical instrument tools and imaging tools. An operator may use Master control devices that are selectively associated with the tools and the manipulators holding the tools. In such a robotic system, the control of a tool in response to operator manipulation of a master control device may have a number of definable reference frames and corresponding frame transformations to map coordinates in one reference frame to corresponding coordinates in another reference frame. When one or more of the position and/or orientation of the frames and/or frame transformations are unknown, however, precise control of the tools may be difficult to achieve. In such cases, the success rate and accuracy of the procedure may be reduced. In a medical robotic context, greater ease and efficacy may be achieved with more precise control of the tools.

In a teleoperational medical system including multiple manipulator assemblies, it is desirable to know the position and/or orientation of the manipulator assemblies relative to each other. Such information can be used, for example, for enhanced operation or collision avoidance. In some teleoperational medical systems, the manipulator assemblies share a known reference, such common mounting base, thus making it possible to derive the relative positions of the manipulator assemblies (and their end effectors) using kinematic relationships between the manipulator assemblies and their known reference.

In some cases, a teleoperational medical system includes independent manipulator assemblies that do not share a known reference (e.g., manipulator assemblies on separately movable carts or mounted to a common table at different unknown locations). In such systems, one or more parameters related to the positioning or orienting of the respective bases of the manipulator assemblies relative to each other is unknown, or may change between procedures or during a procedure (e.g., if the mounting base locations are moved). Thus, while the kinematics of each manipulator may provide information about its individual location or orientation relative to its own base, such individual manipulator kinematics may not provide the manipulator assemblies' orientations and positions relative to each other. Accordingly, it would be advantageous to provide improved methods and systems for registering independent manipulator assemblies of a robotic system, e.g., a teleoperational medical system.

SUMMARY

Embodiments of the invention are described by the claims that follow the description.

Consistent with some embodiments, A robotic system includes first and second manipulator assemblies in an operating environment and having separately movable bases. A processing unit is configured to receive first sensor data from a first plurality of sensors disposed on the first manipulator assembly, wherein the first sensor data provide spatial information about the operating environment external to the first manipulator assembly. A first spatial relationship of the second manipulator assembly relative to the first manipulator assembly is determined using data including the first sensor data. A first alignment relationship between the first and second manipulator assemblies is established based on the first spatial relationship. Based on the first alignment relationship, motion of the second manipulator assembly is commanded in response to a command from a first input device operable by an operator.

Consistent with other embodiments, a method of operating a robotic system, includes receiving first sensor data from a first plurality of sensors disposed on a first manipulator assembly in an operating environment. The first sensor data provides spatial information about the operating environment external to the first manipulator assembly. The first manipulator assembly includes a first plurality of links physically coupled to a first base. The operating environment includes a second manipulator assembly comprising a second plurality of links physically coupled to a second base, the second base separately movable relative to the first base. The method further includes determining a first spatial relationship between the first and second manipulator assemblies using data including the first sensor data, establishing a first alignment relationship between the first and second manipulator assemblies based on the first spatial relationship, and commanding, based on the first alignment relationship, motion of the second manipulator assembly in response to a command from a first input device operated by an operator.

Other embodiments include corresponding computer systems, apparatus, and computer programs recorded on one or more computer storage devices, each configured to perform the actions of the methods.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

Figure 4A:
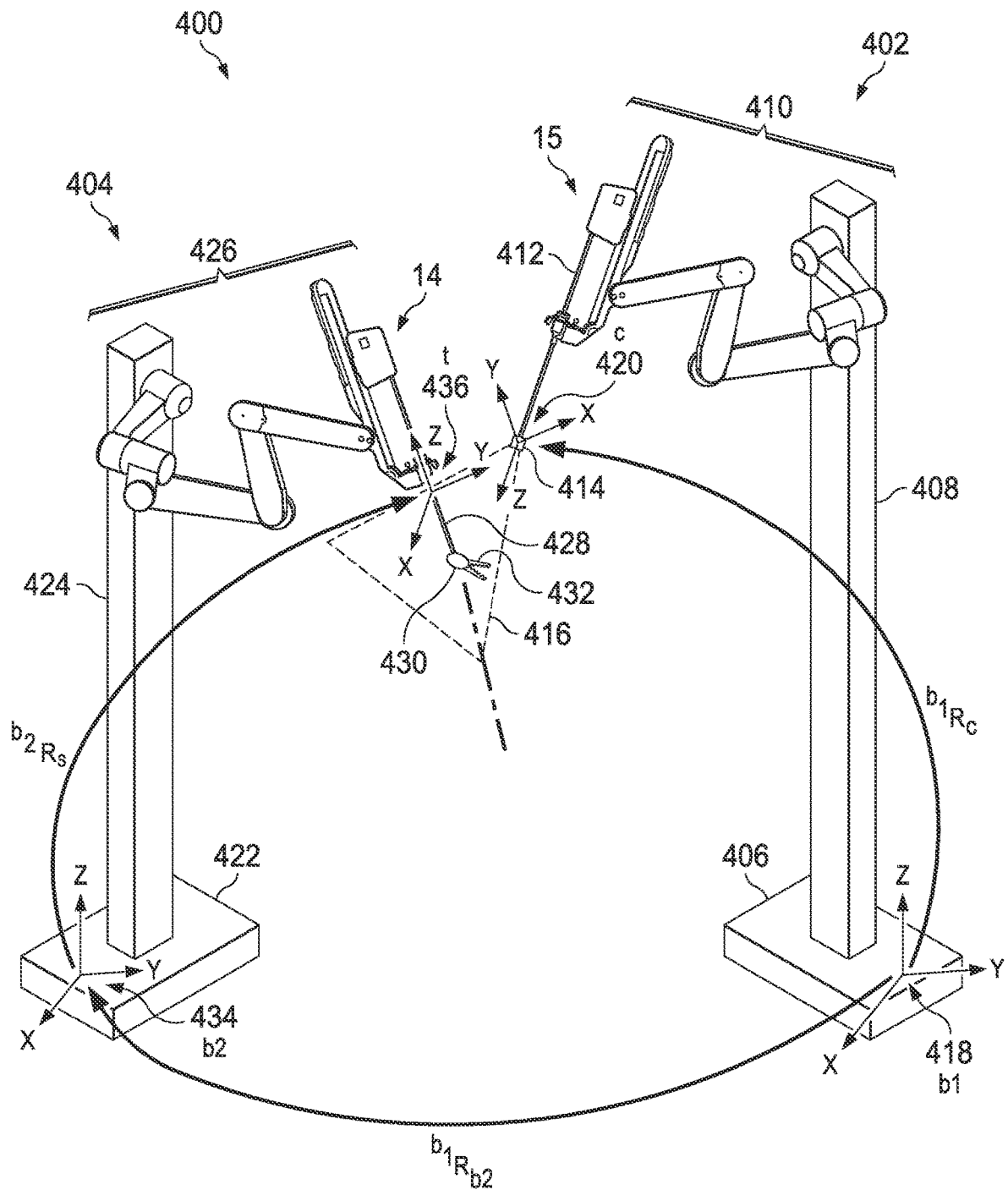
Figure 4B:
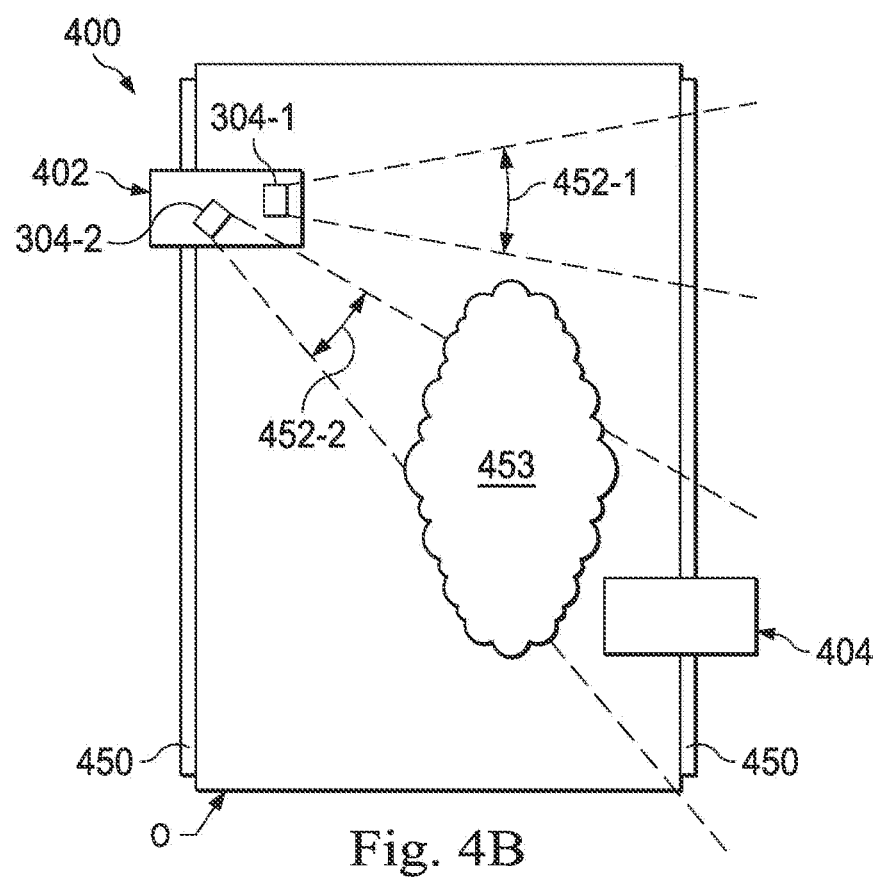
Figure 4C:
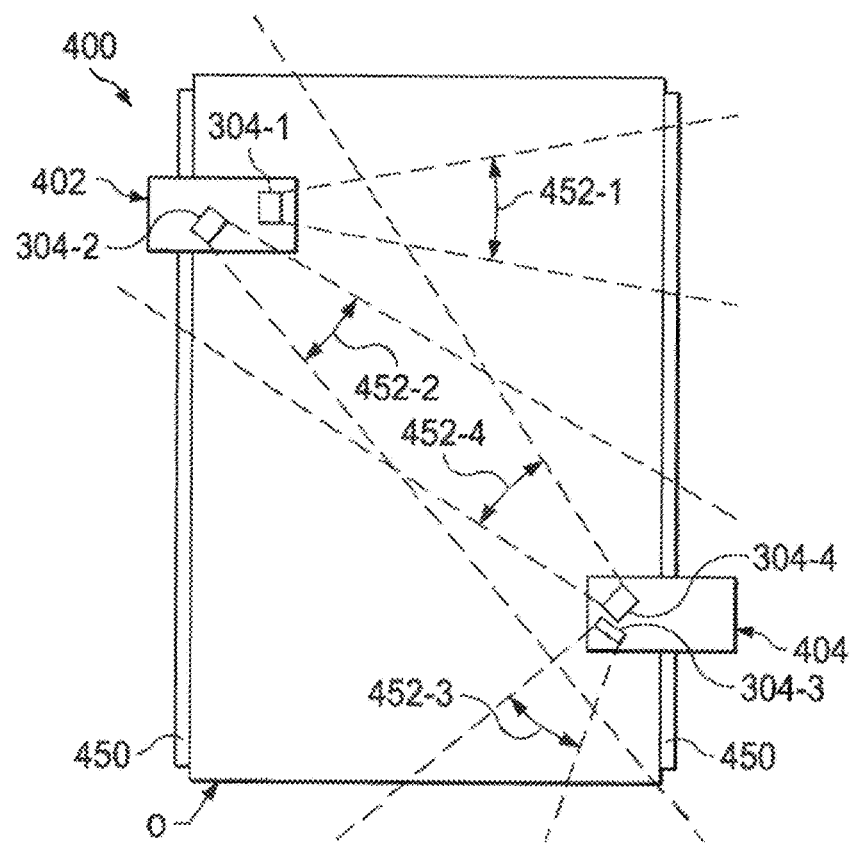
Figure 4D:
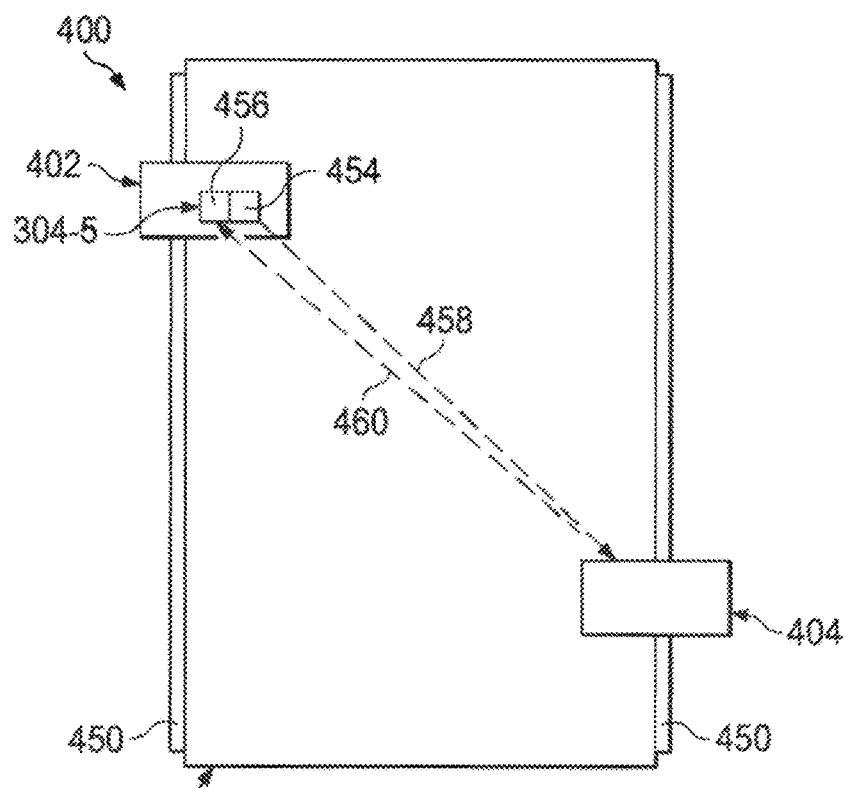
Figure 4E:
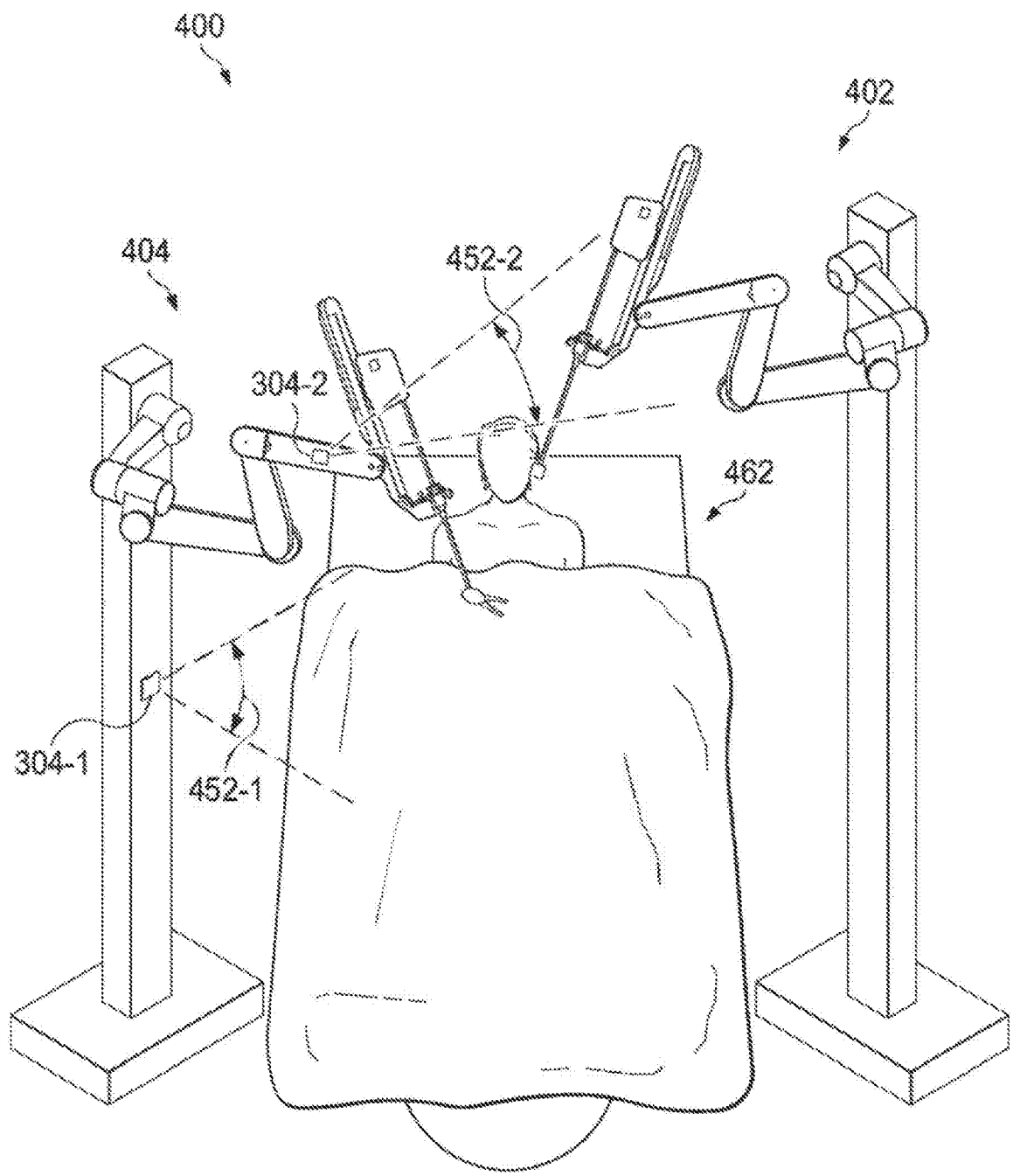

FIG. 4A is a perspective view of two manipulator assemblies, in accordance with an embodiment of the present disclosure; FIG. 4B is a top view of the two manipulator assemblies of FIG. 4A, in accordance with an embodiment of the present disclosure; FIG. 4C is a top view of the two manipulator assemblies of FIG. 4A, in accordance with another embodiment of the present disclosure; FIG. 4D is a top view of the two manipulator assemblies of FIG. 4A, in accordance with yet another embodiment of the present disclosure. FIG. 4E is a schematic view of the two manipulator assemblies of FIG. 4A, in accordance with yet another embodiment of the present disclosure.

Figure 5A:
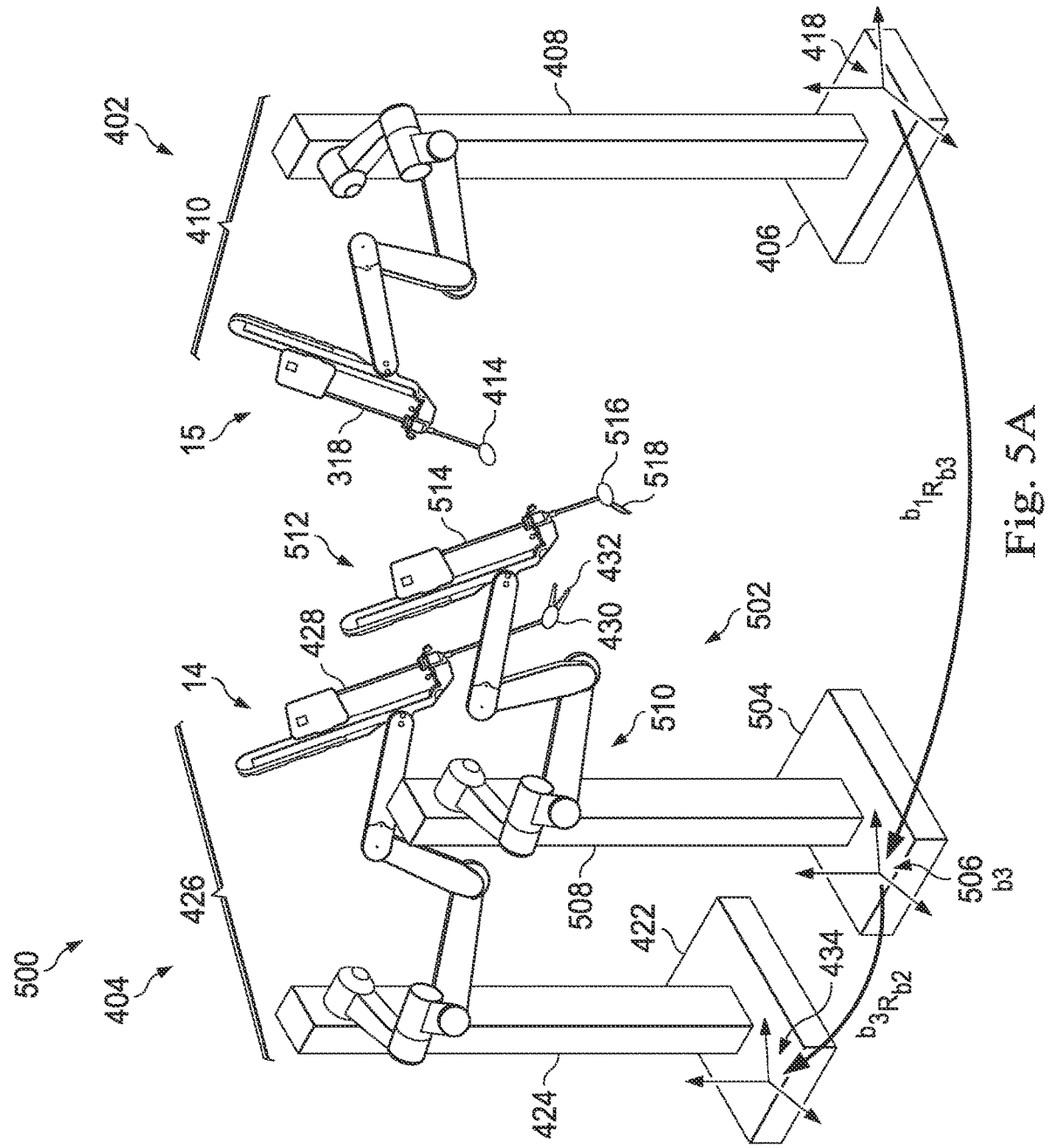
Figure 5B:
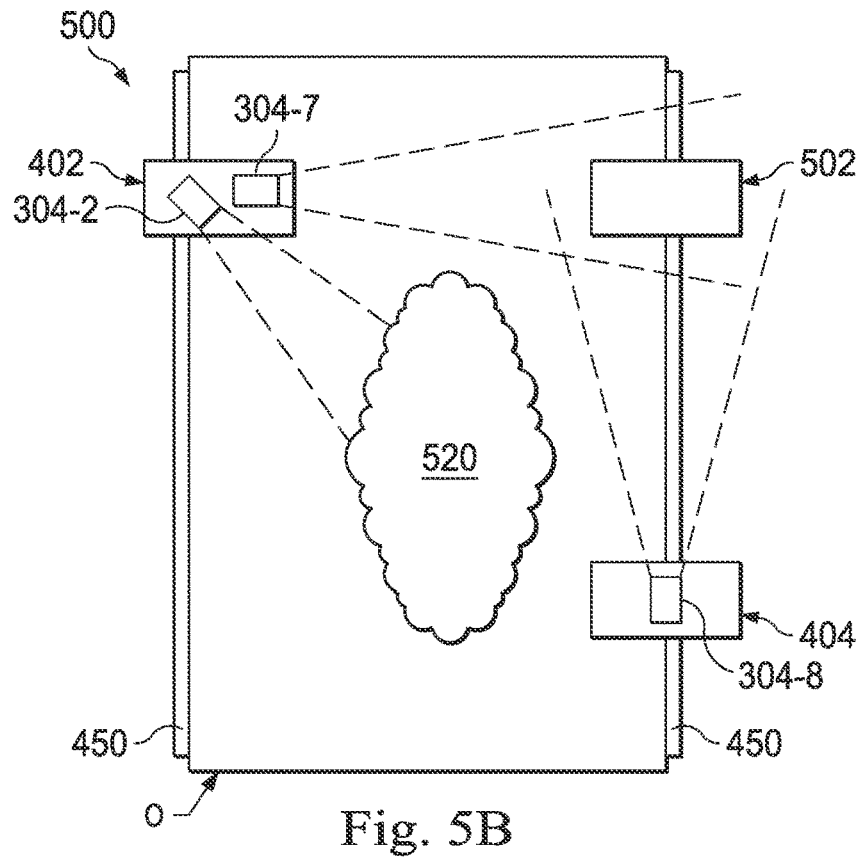
Figure 5C:
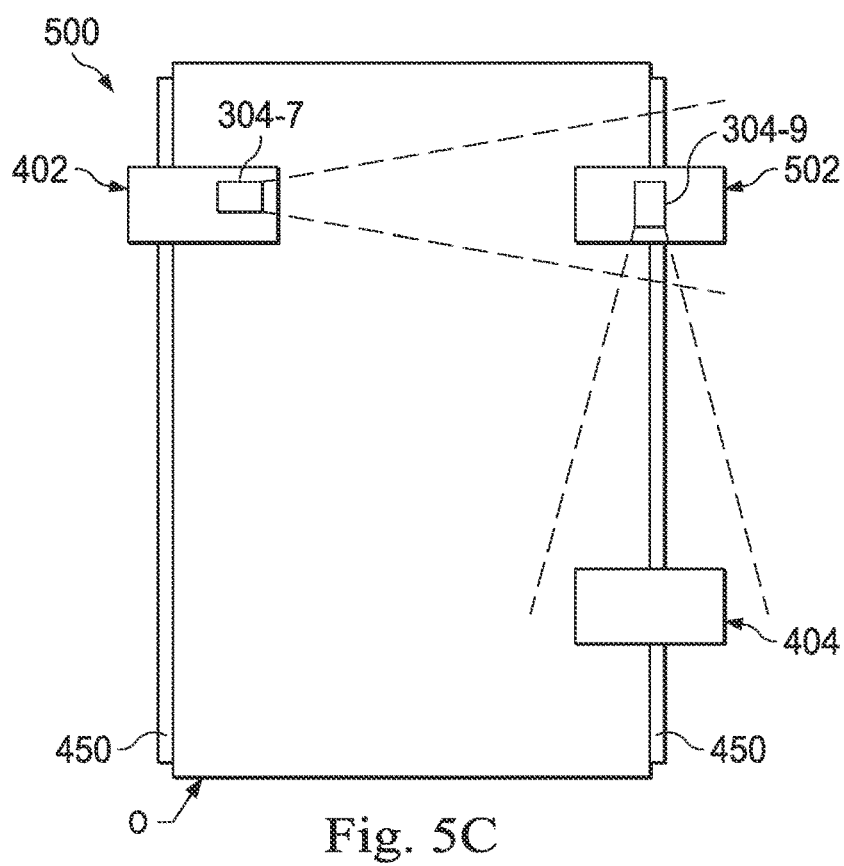
Figure 5D:
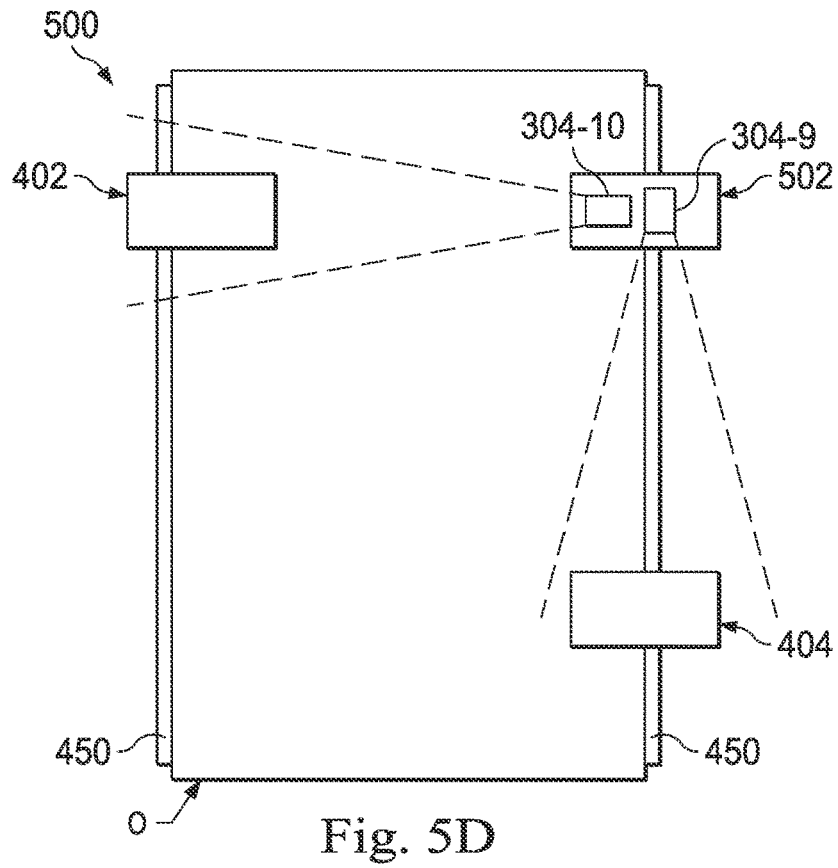
Figure 5E:
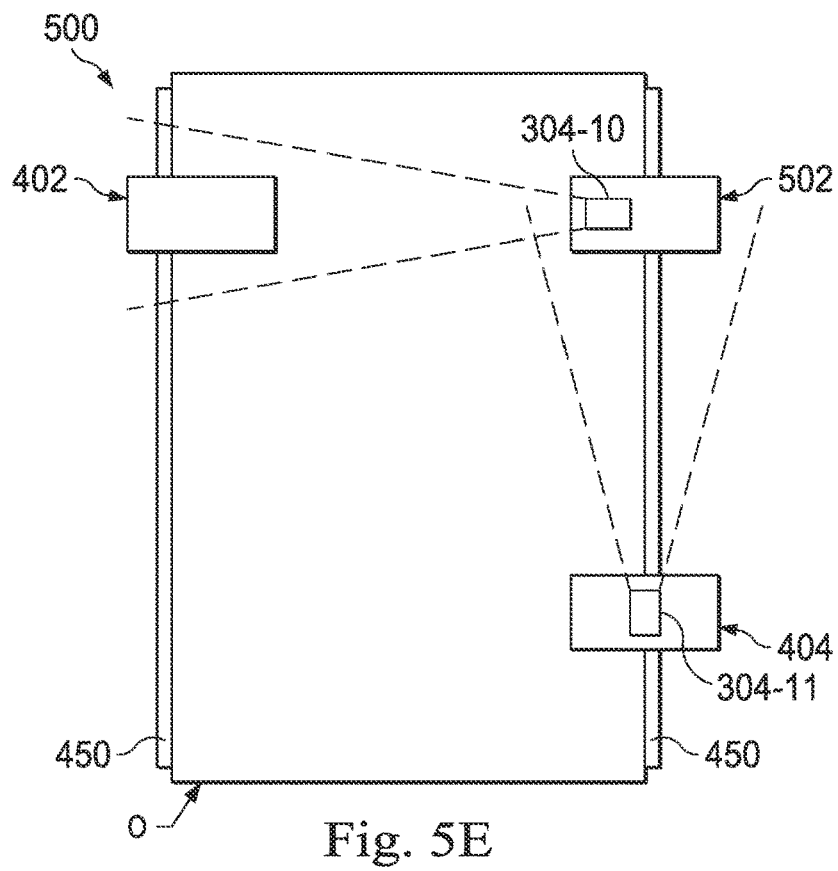

FIG. 5A is a perspective view of three manipulator assemblies, in accordance with an embodiment of the present disclosure; FIG. 5B is a top view of the three manipulator assemblies of FIG. 5A in accordance with an embodiment of the present disclosure; FIG. 5C is a top view of the three manipulator assemblies of FIG. 5A in accordance with another embodiment of the present disclosure; FIG. 5D is a top view of the three manipulator assemblies of FIG. 5A in accordance with yet another embodiment of the present disclosure; FIG. 5E is a top view of the three manipulator assemblies of FIG. 5A in accordance with yet another embodiment of the present disclosure.

Figure 6:
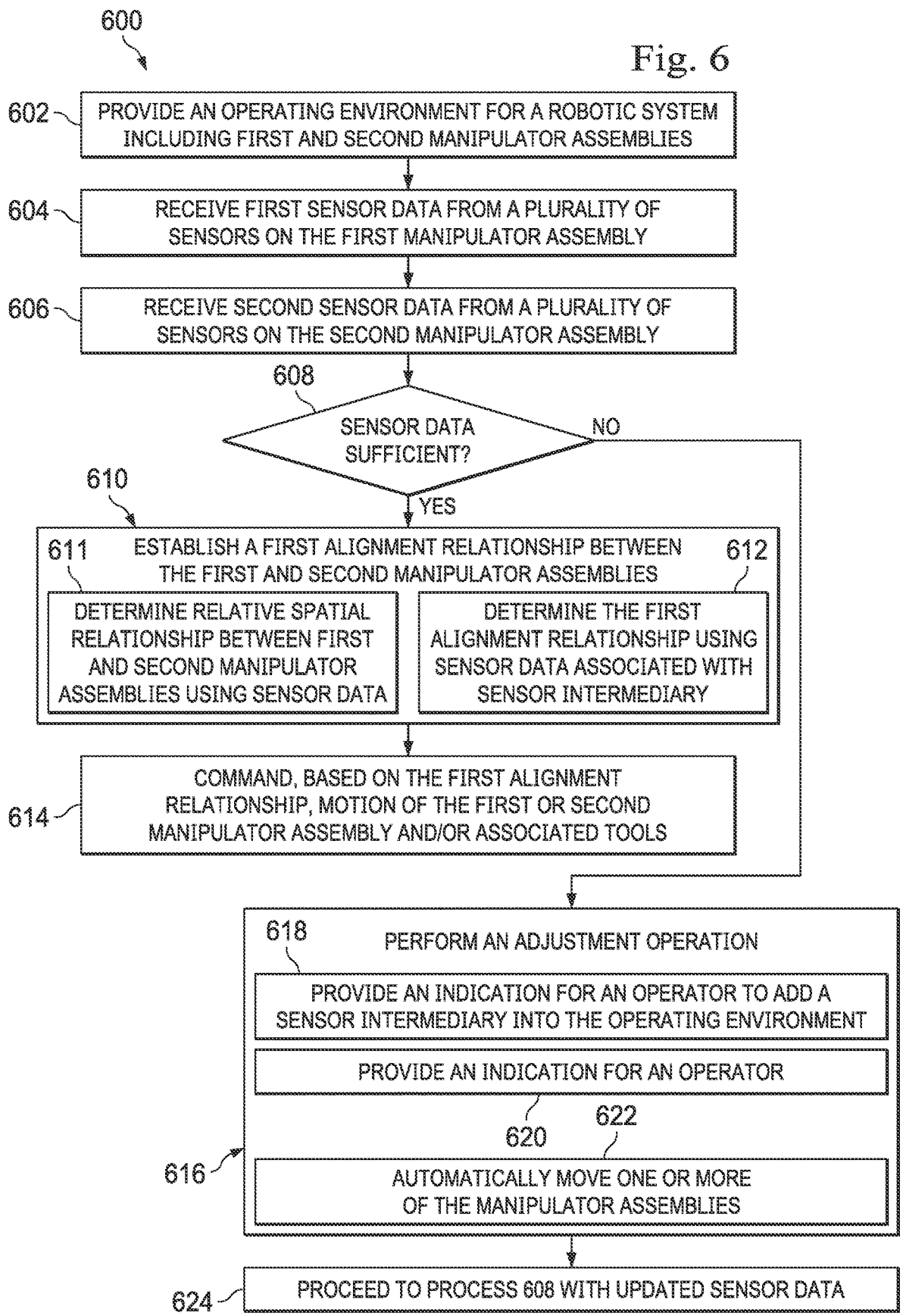

FIG. 6 illustrates a flowchart providing a method for performing a registration process for manipulator assemblies that are separately movable relative each other, in accordance with another embodiment of the present disclosure.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the disclosure, numerous specific details are set forth in order to provide a thorough understanding of the disclosed embodiments. However, it will be obvious to one skilled in the art that the embodiments of this disclosure may be practiced without these specific details. In other instances, well-known methods, procedures, components, and circuits have not been described in detail so as not to unnecessarily obscure aspects of the embodiments of the disclosure.

Any alterations and further modifications to the described devices, tools, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances, the same reference numbers are used throughout the drawings to refer to the same or like parts.

Although some of the examples described herein often refer to surgical procedures or tools, or medical procedures or tools, the techniques disclosed also apply to non-medical procedures and non-medical tools. For example, the tools, systems, and methods described herein may be used for non-medical purposes including industrial uses, general robotic uses, and sensing or manipulation of non-tissue work pieces. Other example applications involve surgical or non-surgical cosmetic improvements, imaging of or gathering data from human or animal anatomy, training medical or non-medical personnel, performing procedures on tissue removed from human or animal anatomies (without return to a human or animal anatomy), and performing procedures on human or animal cadavers.

The embodiments below will describe various tools and portions of tools in terms of their state in three-dimensional space. As used herein, the term "position" refers to the location of an object or a portion of an object in a three-dimensional space (e.g., three degrees of translational freedom that can be described using changes in Cartesian X, Y, Z coordinates, such as along Cartesian X, Y, Z axes). As used herein, the term "orientation" refers to the rotational placement of an object or a portion of an object (three degrees of rotational freedom—e.g., which can be described using roll, pitch, and yaw). As used herein, the term "pose" refers to the position of an object or a portion of an object in at least one degree of translational freedom, and to the orientation of that object or that portion of that object in at least one degree of rotational freedom. For an asymmetric, rigid body in a three-dimensional space, a full pose can be described with six parameters in six total degrees of freedom.

Figure 1:
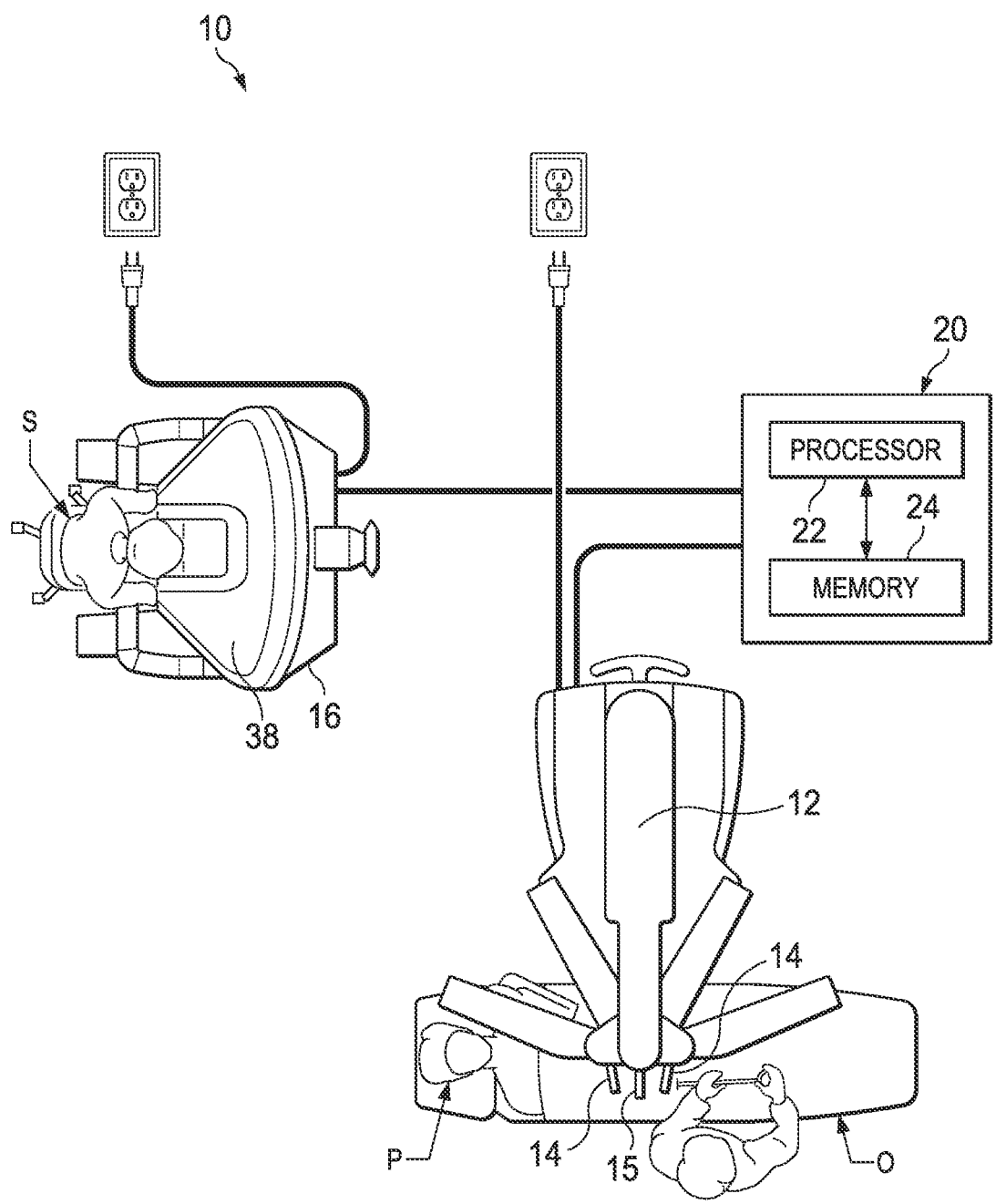
FIG. 1 is a schematic view of a robotic medical system, in accordance with an embodiment of the present disclosure.

Referring to FIG. 1 of the drawings, an example robotic system is shown. Specifically, in FIG. 1, a computer-aided, robotic medical system that may be teleoperated and used in, for example, medical procedures including diagnostic, therapeutic, or surgical procedures, is generally indicated by the reference numeral 10. As will be described, the teleoperational systems of this disclosure are under the teleoperational control of an operator. In some embodiments, manipulators or other parts of a robotic system may be controlled directly through manual interaction with the manipulators (or the other parts) themselves. Thus, "teleoperated manipulators" as used in this application include manipulators that can be controlled partially or entirely through teleoperation, and include manipulators that can be controlled through both teleoperation and direct manual control simultaneously or in a time multiplexed manner. Further, in some embodiments, a non-teleoperational or robotic medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures.

As shown in FIG. 1, the robotic medical system 10 generally includes a manipulator assembly 12 mounted to or near an operating table O on which a patient P is positioned. The manipulator assemblies described herein often include one or more robotic manipulators and tools mounted thereon, although the term "manipulator assembly" also encompasses the manipulator without the tool mounted thereon. The manipulator assembly 12 may be referred to as a patient side cart in this example, since it comprises a cart and is designed to be used next to a patient. A medical tool 14 (also referred to as a tool 14) and a medical tool 15 are operably coupled to the manipulator assembly 12. Within this disclosure, the medical tool 15 includes an imaging device, and may also be referred to as the imaging tool 15. The imaging tool 15 may comprise an endoscopic imaging system using optical imaging technology, or comprise another type of imaging system using other technology (e.g. ultrasonic, fluoroscopic, etc.). An operator input system 16 allows an operator such as a surgeon or other type of clinician S to view images of or representing the procedure site and to control the operation of the medical tool 14 and/or the imaging tool 15.

The operator input system 16 for the robotic medical system 10 may be "mechanically grounded" by being connected to a base with linkages such as to an operator's console, or it may be "mechanically ungrounded" and not be thus connected. As shown in FIG. 1, the operator input system 16 is connected to an operator's console 38 that is usually located in the same room as operating table O during a surgical procedure. It should be understood, however, that the operator S can be located in a different room or a completely different building from the patient P. The operator input system 16 generally includes one or more control device(s) for controlling the medical tool 14. The operator input system 16 is also referred to herein as "master manipulators," "master control devices," "master input devices," and "input devices." The control device(s) may include one or more of any number of a variety of input devices, such as hand grips, joysticks, trackballs, data gloves, trigger-guns, foot pedals, hand-operated controllers, voice recognition devices, touch screens, body motion or presence sensors, and the like. In some embodiments, the control device(s) will be provided with the same degrees of freedom as the medical tools of the robotic assembly to provide the operator with telepresence; that is, the operator is provided with the perception that the control device(s) are integral with the tools so that the operator has a sense of directly controlling tools as if present at the procedure site. In other embodiments, the control device(s) may have more or fewer degrees of freedom than the associated medical tools and still provide the operator with telepresence. In some embodiments, the control device(s) are manual input devices which move with six degrees of freedom, and which may also include an actuatable handle for actuating medical tools (for example, for closing grasping jaw end effectors, applying an electrical potential to an electrode, capture images, delivering a medicinal treatment, and the like).

The manipulator assembly 12 supports and manipulates the medical tool 14 while the operator S views the procedure site through the operator's console. An image of the procedure site can be obtained by the medical tool 15, such as via an imaging system comprising a monoscopic or stereoscopic endoscope, which can be manipulated by the manipulator assembly 12 to orient the medical tool 15. An electronics cart can be used to process the images of the procedure site for subsequent display to the operator S through the operator's console. The number of medical tools 14 used at one time will generally depend on the medical diagnostic or treatment (e.g. surgical) procedure and the space constraints within the operating room among other factors. The manipulator assembly 12 may include a kinematic structure of one or more links coupled by one or more non-servo controlled joints, and a servo-controlled robotic manipulator. In various implementations, the non-servo controlled joints can be manually positioned or locked, to allow or inhibit relative motion between the links physically coupled to the non-servo controlled joints. The manipulator assembly 12 includes a plurality of motors that drive inputs on the medical tools 14. These motors move in response to commands from the control system (e.g., control system 20). The motors include drive systems which when coupled to the medical tools 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the tool for grasping tissue in the jaws of a biopsy device or the like. The medical tools 14 may include end effectors having a single working member such as a scalpel, a blunt blade, a needle, an imaging sensor, an optical fiber, an electrode, etc. Other end effectors may include multiple working members, and examples include forceps, graspers, scissors, clip appliers, staplers, bipolar electrocautery instruments, etc.

The robotic medical system 10 also includes a control system 20. The control system 20 includes at least one memory 24 and at least one processor 22, and typically a plurality of processors, for effecting control between the medical tool 14, the operator input system 16, and other auxiliary systems 26 which may include, for example, imaging systems, audio systems, fluid delivery systems, display systems, illumination systems, steering control systems, irrigation systems, and/or suction systems. The control system 20 also includes programmed instructions (e.g., a computer-readable medium storing the instructions) to implement some or all of the methods described in accordance with aspects disclosed herein. While control system 20 is shown as a single block in the simplified schematic of FIG. 1, the system may include two or more data processing circuits with one portion of the processing optionally being performed on or adjacent the manipulator assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 20 supports wireless communication protocols such as Bluetooth, IrDA, HomeRF, IEEE 802.11, DECT, and Wireless Telemetry.

In some embodiments, the control system 20 may include one or more actuator controllers that receive force and/or torque feedback from the medical tool 14 or from the manipulator assembly 12. Responsive to the feedback, the actuator controllers transmit signals to the operator input system 16. The actuator controller(s) may also transmit signals that instruct the manipulator assembly 12 to move the medical tool(s) 14 and/or 15 which extends into an internal procedure site within the patient body via openings in the body. Any suitable conventional or specialized controller may be used. A controller may be separate from, or integrated with, manipulator assembly 12. In some embodiments, the controller and manipulator assembly are provided as part of an integrated system such as a teleoperational arm cart positioned proximate to the patient's body during the medical procedure.

The control system 20 can be coupled to the medical tool 15 and can include a processor to process captured images for subsequent display, such as to an operator using the operator's console or wearing a head-mounted display system, on one or more stationary or movable monitors near the control system, or on another suitable display located locally and/or remotely. For example, where a stereoscopic endoscope is used, the control system 20 can process the captured images to present the operator with coordinated stereo images of the procedure site. Such coordination can include alignment between the stereo images and can include adjusting the stereo working distance of the stereoscopic endoscope.

In alternative embodiments, the robotic system may include more than one manipulator assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

In various embodiments, the operator's console 38 includes a left eye display and a right eye display for presenting the operator S with a coordinated stereo view of the surgical environment that enables depth perception. An operator input system 16 of the operator's console 38 includes one or more input control devices, which in turn causes the manipulator assembly 12 to manipulate one or more medical tools 14 and/or 15. The input control devices may be used to, for example, close grasping jaw end effectors, apply an electrical potential to an electrode, deliver a medicinal treatment, or the like. In various alternatives, the input control devices may additionally or alternatively include joystick devices, trackballs, data gloves, trigger-guns, hand-operated controllers, voice recognition devices, touch screens, body motion or presence sensors, and the like. In some embodiments and for some associated medical tools 14, the input control devices will provide the same degrees of freedom as their associated medical tools 14 to provide the operator S with telepresence, or the perception that the input control devices 36 are integral with the tools 14 so that the operator S has a sense of directly controlling the tools 14. In other embodiments, the input control devices may have more or fewer degrees of freedom than the associated medical tools and still provide the operator S with telepresence. To this end, position, force, and tactile feedback sensors may be employed to transmit position, force, and tactile sensations from the tools 14 back to the operator S's hands through the input control devices. An operator input system 16 of the operator's console 38 may also include input control devices including foot pedals that receive input from a user's foot.

Figure 2:
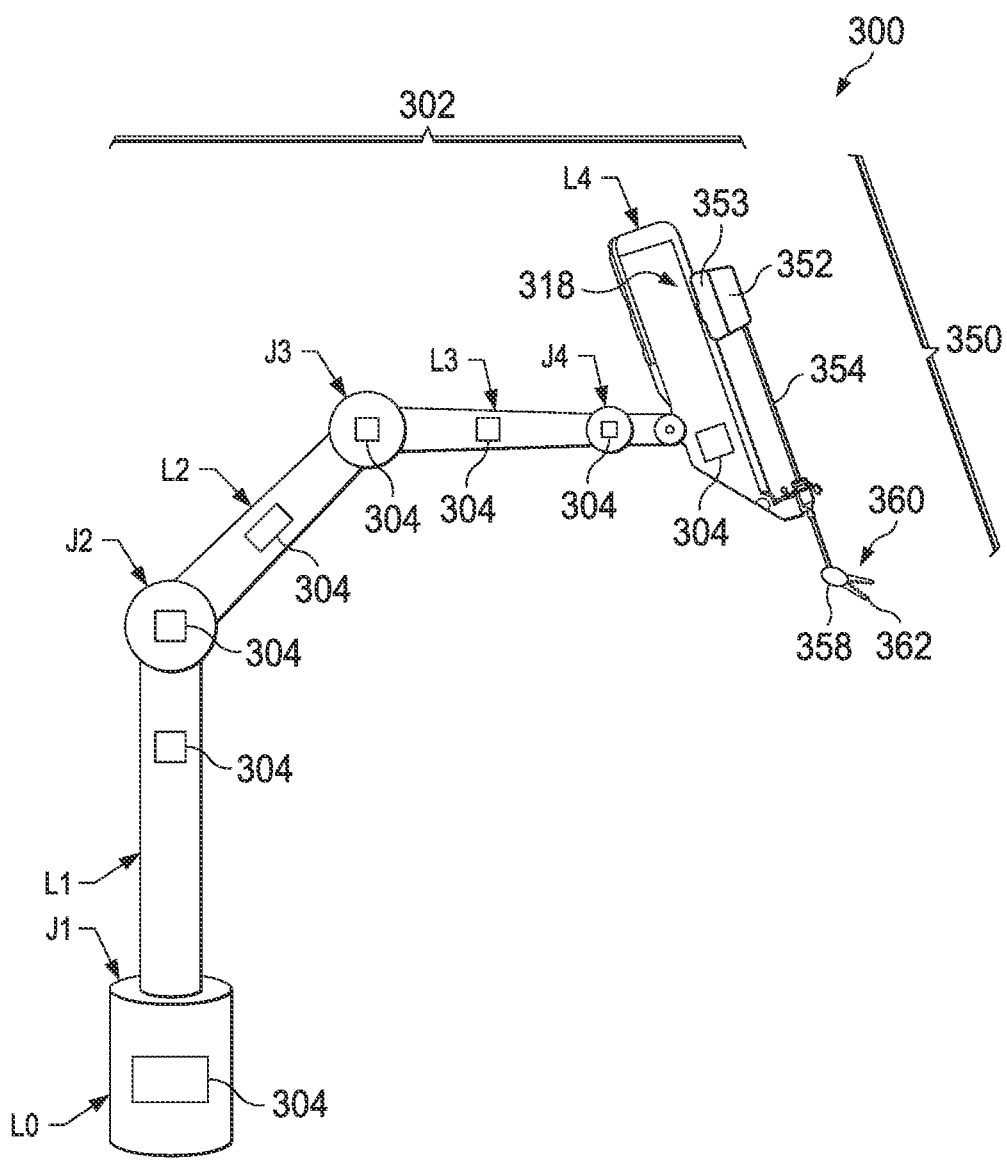
FIG. 2 is a perspective view of a manipulator assembly with an external environment detection sensor system, in accordance with an embodiment of the present disclosure.

Referring now to FIG. 2, a manipulator assembly 300 with a single manipulator 302 is illustrated. The manipulator assembly 300 may be configured in the form of a patient side cart (e.g., a manipulator assembly 12 for the example of FIG. 1), or be mounted to a patient table or table rail (e.g. a surgical table, an examination table), to a ceiling mount, to a wall mount, or to a floor mount. In the example of FIG. 2, the manipulator assembly 300 includes the manipulator 302, and shows an interchangeable tool 350 mounted on the manipulator 302. The manipulator 302, and the tool 350 may also be referred herein as an instrument 350.

In some embodiments, the tool 350 may be configured for manipulating industrial work pieces, or to manipulate human or animal tissue for reasons other than medical treatment or diagnosis. In some embodiments, the tool 350 may comprise a tool for performing medical procedures. The tool 350 includes a mounting portion 352 and a shaft 354. In the example shown in FIG. 2, the mounting portion 352 comprises a mount located on a proximal portion of the tool 350. As used herein, the term proximal generally refers to a direction or position away from the work piece or patient, and distal generally refers to a direction or position closer to the work piece or patient. The mount is configured for removably coupling the tool 350 to a fifth joint that enables the movement of the carriage 353 of the manipulator 302. As shown in FIG. 2, this fifth joint includes a prismatic joint aligned along an insertion direction of the tool 350. The shaft 354 is coupled to an end effector 360 using a wrist 358. The end effector 360 has a tool tip 362. In some embodiments, the manipulator assembly 300 may include a support for a port device (e.g. a cannula for some medical procedures) that guides or limits movement of the tool 350 relative to the manipulator assembly 300. The tool 350 associated with each manipulator assembly 300 may also be controlled by the operator at an operator input system (e.g. the operator input system 16 for the example of FIG. 1).

In more detail, the example manipulator 302 includes links L1, L2, L3, L4, and a fifth link (e.g., denoted as L5 including the carriage 353), connected by joints J1, J2, J3, J4, and a fifth joint (e.g., denoted as J5) into a kinematic chain. The tool 350's mounting portion 352 is mounted to L5, which is physically coupled to link L4. Each of the joints (e.g., J1, J2, J3, J4, and J5) are controlled by motors. In an example, movement of J5 moves L5 relative to L4, and provides insertion and withdrawal motion to the tool 350. Other manipulator designs may not have such an J5 enabling a moveable carriage 353; or, other manipulator designs may not have a carriage 353 at all and couple with the tool 350 in another manner, and the manipulator inserts and withdraws the tool 350 by moving one or more other joints (e.g. joints J2-J4). Accordingly, at least parts of the manipulator assembly 300 are configured to move using motorized or active joints. In this embodiment, the motors of the manipulator 302 are under the control of the control system (e.g., the control system 20) and may be operated in coordination with motors of other manipulator(s) of the same manipulator assembly 300 if the manipulator assembly 300 has other manipulator(s), or in coordination with other manipulator assemblies, to take desired poses that may assist with advancing over a work piece (or a patient in a medical procedure), mounting of tools, preparation steps, storage, moving to target anatomy inside a patient's body and manipulating tissue, placing the remote center of motion, making space for assistants, obstacles, or equipment around the patient, applying forces to anatomical structures such as for palpating tissue, among other activities. In addition, encoders and other sensors associated with each motor or joint of the manipulator assembly 200 provide feedback to the control system so that the control system receives data about, senses or detects, or determines the motion state of the joint/motor, status, torques applied by or on the joints, and setup of the manipulator assembly 300.

Although each of the joints (e.g., J1, J2, J3, J4, and J5) may be controlled by an individual or a plurality of joint or actuator controller(s), the joint and actuator controllers may be controlled by a common joint control unit of a common control system (e.g., control system 20, a master/slave control system, etc.). Thus, the tool 350, the tip 362 and end effector 360 of the tool 350, and the manipulator 302 may be controlled through user (e.g., Operator S) manipulation of its associated control device (e.g., the operator input system for the example of FIG. 1).

It is noted that the kinematic configuration of the manipulator assembly 300 illustrated in FIG. 2 is exemplary only and not intended to be limiting beyond what is specifically recited in the claims that follow. It will be understood by those skilled in that art in possession of this disclosure that other configurations may be used. For example, one or more of the joints (e.g., joints J1, J2, J3, J4, J5) may be non-servo controlled, and may be configured such that they can be manually positioned or locked. As another example, the manipulator assembly 300 may include different numbers, types (e.g., rotary joints, prismatic joints), and combinations of joints. In one example, the manipulator assembly 300 may include a parallelogram linkage. In another example, the manipulator assembly 300 may include a prismatic joint proximal to a base link L0, and one or more rotational joints distal to the base link L0. In that example, the one or more rotational joints distal to a base link L0 may rotate in a particular plane or in three dimensions. In yet another example, the manipulator assembly 300 may include a single-port platform including a base manipulator carrying a plurality of sub-manipulators. In that example, each of the sub-manipulator may be serially connected to the base manipulator.

In the example of FIG. 2, an external environment detection sensor system 304 (also referred to as external environment sensor system 304 or sensor system 304) is attached to the manipulator assembly 300. In various examples, sensors of the external environment detection sensor system 304 may be located at one or more of the links (L0, L1, L2, L3, L4, or L5) and joints (J1, J2, J3, J4, or J5) of the manipulator assembly 300. In some examples where the manipulator assembly 300 includes a clamp, the sensor(s) of the manipulator assembly may be coupled to the clamp.

The external environment detection sensor system 304 may provide information (e.g., to control system 20) regarding environment external to the manipulator assembly 300. The external environment detection sensor system 304 may include one or more sensors including, for example, optical sensors, depth sensors, time of flight sensors, emitter-receiver sensors, any other suitable sensors, and/or a combination thereof. In some examples, the optical sensors include imaging devices that detect visible light or non-visible light. The optical sensor would detect images of other manipulator assemblies, and process the resulting images to identify and locate portions of external objects (e.g., other manipulator assemblies). For example, different manipulator assemblies may be identified by markings, colors, shapes, supported tool, movement specific to the manipulator assembly that's visible to such sensors. Depth information may be provided by integrated or separate depth sensors, triangulation through use of multiple imaging devices or stereoscopic imaging devices, or any appropriate technique. In some examples, time of flight sensors include laser rangefinder, LED rangefinder, lidar, radar, etc. In embodiments when the sensors include optical sensors or time of flight sensors, the control system may detect and process occlusion, because those sensors may provide information of an external object only when they are able to view at least a portion of the external object.

In some embodiments, the sensors may include accelerometers, electromagnetic sensors, RFID sensors, inclinometers, or inertial measurement units (IMUs). Accelerometers, inclinometers and IMUs may not directly provide manipulator assembly-to-manipulator assembly registration data; instead, they may be used to provide orientation information relative to a world frame, which can be used to provide some of the rotational transform between manipulator assemblies, or as a check against the rotational transform otherwise calculated.

In various embodiments, the manipulator assembly 300 may have different external environment detection sensor system arrangements. In the example of FIG. 2, the manipulator assembly 300 may include a plurality of sensors, each located a different link or joint of the manipulator assembly 300 respectively. In some examples, a single link or joint may have multiple sensors of the external environment detection sensor system 304. Note that while in FIG. 2, an external environment detection sensor system 304 is attached to each link (or a tool rigidly mounted to the link) and each joint of a manipulator 302, in some embodiments, the manipulator 302 may include links and/or joints that do not have any external environment detection sensor system attached thereon.

As shown in the example of FIG. 2, different tools 350 and/or end effectors 360 may be mounted to the manipulator assembly 300 to perform different functions. In that example, those external environment detection sensor system 304 attached to the manipulator 302 may be used in providing data for controlling movement of different tools 350 and/or end effectors 360.

In some embodiments, the sensor data provided by external environment detection sensor system 304 include spatial information of a detected external object (e.g., another manipulator assembly) relative to the manipulator assembly 300. In some examples, the sensor data includes one or more images detected by one or more image sensors of the external environment detection sensor system 304 respectively. In some examples, the sensor data may also include identification information used to identify the detected external object (e.g., another manipulator assembly). In some examples, the sensor data may include identification information used to identify a sensor location (e.g., a link of the manipulator assembly).

In various embodiments, image sensors described herein may include various sensors for various types of sensing technologies that may be used to provide images of various dimensions (e.g., images of two dimensions (2D), three dimensions (3D), or any other suitable higher dimensional representation of a space). In various examples, a 3D image may be provided, e.g., directly by a 3D image sensor, constructed from a series of 2D sensor information and any/or other suitable sensor information, and/or using any other suitable techniques. For example, a 3D image may be constructed from 2D sensor information use depth information including depth map. In various examples, the depth information may be provided by various techniques, including, for example, stereo images, depth cameras, laser ranging techniques, etc. As such, image sensors described herein may include any sensor configured to generate a 2D, 3D, or higher dimensional representation of the space, including e.g., capacitive sensors designed to provide a capacitive 2D representation of the capacitance in an area (e.g. a touchscreen on a cellphone), liquid level sensors, switches, IR cameras, LIDARs, depth cameras, radars, sonars, ultrasonic sensors, optical cameras, any other suitable sensors, and/or a combination thereof.

As described below with reference to FIGS. 3-6, in an environment including multiple manipulator assemblies having separately movable bases, a control system (e.g. the control system 20 for the example of FIG. 1) may receive sensor data including environment information external to corresponding manipulator assemblies. Such sensor data may be provided by one or more external environment detection sensor systems on the corresponding manipulator assemblies, and the control system may use the sensor data to perform registration of the multiple manipulator assemblies. Such registration may be used to control those manipulator assemblies and/or associated tools, and provide enhanced operation and/or collision avoidance. In some embodiments, the sensor data (e.g., that is used for registration) are used to determine environmental information such as locations or shapes of non-manipulator items (e.g., obstacles including for example one or more operators or patient). Such determination may be performed in a continuous or periodic way, and provide dynamic and/or real time detection of the obstacles, which may be further used for enhanced operation, collision avoidance, etc.

Figure 3:
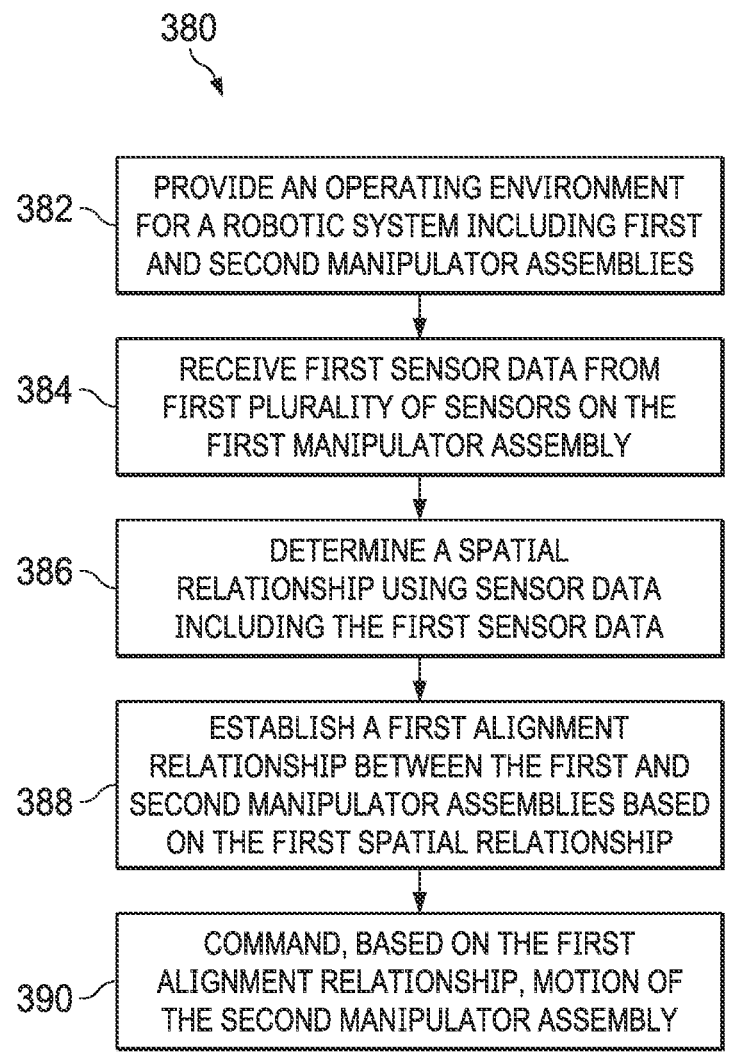
FIG. 3 illustrates a flowchart providing a method for performing a registration process for manipulator assemblies that are separately movable relative each other, in accordance with an embodiment of the present disclosure.

Referring to the example of FIG. 3, a flowchart provides a method 380 for performing a registration process for manipulator assemblies that are separately movable relative each other. The method 380 begins at process 382, where an operating environment in which a robotic system operates is provided, and the robotic system includes first and second manipulator assemblies having separately movable bases. The method 380 may proceed to process 384, where a control system receives sensor data including first sensor data from a plurality of sensors on the first manipulator assembly to provide the operating environment external to the first manipulator assembly. The method 380 may proceed to process 386, where the control system determines a spatial relationship between the first and second manipulator assemblies using sensor data including the first sensor data. The method 380 may then proceed to process 388, where the control system establishes a first alignment relationship (e.g., a transformation for registration) between the first and second manipulator assemblies based on the first spatial relationship. The method 380 may the proceed to process 390, where the control system switches from a registration mode (e.g., including processes 382-388) to a tool control mode (e.g., in a medical example, to perform an action on a patient on the operating table during a medical procedure). When operating in the tool control mode, the control system may control the movement of the second manipulator assembly or associated tool therein relative to a reference frame of an imaging device (also referred to as the "imaging device frame") in response to movement of a master control device associated with that tool.

Referring to the examples of FIGS. 4A, 4B, 4C, 4D, and 4E, various configurations of external environment detection sensor systems in a robotic system 400 including two manipulator assemblies having separately movable bases are illustrated. Referring to the example of FIG. 4A, illustrated is a robotic system 400 (e.g., a robotic medical system 10 of FIG. 1) including two manipulator assemblies 402 and 404 on separate bases 406 and 422 respectively. The manipulator assembly 402 includes a base 406, a structure support 408, and a manipulator 410. In the example of FIG. 4A, an imaging tool 15 is mounted on the manipulator 410 and thus the manipulator assembly 402 can be considered to further include the mounted imaging tool 15. The imaging tool 15 includes a shaft 412 and an imaging device 414. The imaging device 414 may include for example an optical imager, an ultrasonic imager, an electromagnetic imager such as a fluoroscopic imager, a thermal imager, a thermoacoustic imager, and any other suitable imagers. The imaging device 414 has a field of view 416.

As illustrated in FIG. 4A, the base 406 has a reference frame 418, which is also referred to as a imaging base frame 418 (denoted as b1). The imaging device 414 has a reference frame 420, which is also referred to as an imaging device reference frame 420 (denoted as c). A transformation from the base reference frame 418 to the imaging device frame 420 is denoted as $^{b1}T_c$, which may be determined based on the forward kinematics of the manipulator assembly 402.

As illustrated in FIG. 4A, the robotic system 400 also includes a manipulator assembly 404. The manipulator assembly 404 includes a base 422 that is physically separate and independent from the base 406 of the manipulator assembly 402. The manipulator assembly 404 includes a structural support 424 and a manipulator 426. In the example of FIG. 4A, a tool 14 is mounted on the manipulator 426, and thus the manipulator assembly 404 can be considered to further include the mounted tool 14. The tool 14 includes a shaft 428, a wrist 430 coupled to the distal end of the shaft 428, and an end effector 432 coupled to the wrist 430. The base 422 has a reference frame 434, which is also referred to as a tool base frame 434 (denoted as b2). The shaft 428 of the tool 14 has a reference frame 436, which is also referred to as a shaft reference frame 436 (denoted as s). A transformation from the tool base frame 434 to the shaft reference frame 436 may be denoted as $^{b2}T_s$, and may be determined (e.g., based on the forward kinematics of the manipulator assembly 404).

In an example, manipulator assemblies 402 and 404 may be disposed in different carts that are moveable relative to each other. In another example, manipulator assemblies 402 and 404 may comprise clamps that allow them to be clamped to different components (e.g. bed frame, bed rail, ceiling fixture, etc.) respectively. In some examples, each manipulator assembly includes a clamp used to removably couple the manipulator assembly to a rail of a surgical table, which allows the manipulator assemblies to be positioned in different configurations around the surgical table depending on the surgical procedure to be performed. In some examples, one or more manipulator assemblies are coupled to respective own mounting systems. In those examples, each manipulator assembly is independently movable relative to the other manipulator assembly and may be positioned next to the surgical table in different configurations around the surgical table depending on the surgical procedure to be performed.

In various embodiments, the positions and orientations of the bases 406 and 422 relative to each other are unknown. As such, the transformation $^{b1}T_{b2}$ from the imaging base frame 418 b1 to the tool base frame 434 b2 is unknown. Such an unknown alignment relationship between the bases 406 and 422 may make intuitive control of a slave tool/end effector by a master control device difficult. To provide an effective control relationship between a master control device and its slave tool/end effector (also referred to as a master-tool alignment), a spatial alignment between the master control device and the tool/end effector is needed. Such a spatial alignment provides a reasonably accurate relationship between the operator's perceived motion of the master control device (e.g., a proprioceptive sense) and the operator's perceived resulting motion of the tool including the shaft and the end effector (e.g., a visual sense). For example, if the operator moves a hand grasping a master control device to the left, the operator expects to perceive the associated slave tool/end effector to move to the left also. If the perceived spatial motions match, then the operator can easily control the slave tool's/end effector's movement by moving the master control device. But if the perceived spatial motions do not match (e.g., a master control device movement to the left results in a slave tool's/end effector's movement up and to the right), then it is difficult for the operator to control the slave's movement by moving the master control device. As described in detail below, a registration process using external environment sensor systems may be used to determine the unknown alignment relationship between the bases 406 and 422 (also referred to as alignment relationship between manipulator assemblies 402 and 404), which may then be used to determine the master-tool alignment and a master-tool transformation.

One or more of the manipulator assemblies 402 and 404 (e.g., a manipulator assembly 300 of FIG. 2) may include a corresponding external environment sensor system (e.g., external environment sensor system 304). The registration process may use sensor data from external environment sensor systems coupled to the manipulator assemblies to determine the manipulator assemblies alignment and master-tool alignment. Additional information (e.g., known kinematic relationships and reference frame transforms in the robotic system) may also be used. In some examples, such additional information may include link data provided to the control system by link sensor systems attached to links of a manipulator and/or attached to a tool supported by the manipulator, where the link data may include, for example, measurements and/or estimates of the state (e.g., pose, velocity, acceleration) of the links. These relationships are described below in Cartesian terms, although other 3-dimensional coordinate systems may be used.

Various configurations of the sensor system 304 may be provided. As shown in FIGS. 4B-4E below, the multiple sensors in a sensor system 304 of a manipulator assembly provide redundancy and redundant data, which alleviate the problems introduced by occlusion, and increase the overall accuracy of the data set. In some examples, manipulator assemblies comprising clamps with sensors are coupled to the same rail of the surgical table (i.e., coupled on the same side of the surgical table). In such examples, the sensors coupled to the clamps of different manipulator assemblies may be within each other's field of view. These sensors may communicate with each other, and/or communicate with the control system, which enables the control system to determine the position of one manipulator assembly relative to another manipulator assembly. The control system may determine those relative positions using the data including the redundant data provided by all sensors (e.g., using kinematic and/or dynamic calculation).

In other examples, the manipulator assemblies are coupled to different rails of the surgical table (i.e., coupled on different or opposite sides of the surgical table). In those examples, there may be an occlusion between some sensors coupled to the clamps of different manipulator assemblies (e.g., a first sensor of a first manipulator assembly is occluded from or outside of a field of view of a second sensor of a second manipulator assembly). However, because of the redundant sensors on each manipulator assembly, other sensors (e.g., coupled to the other joints or links) of the manipulator assemblies are not be occluded from each other, and those non-occluded sensors may provide sufficient spatial relationship information, which enables the control system to determine the spatial relationship of one manipulator assembly relative to another manipulator assembly.

Referring to the example of FIG. 4B, an example of the robotic system 400 with external environment sensor systems is illustrated. Manipulator assemblies 402 and 404 are mounted at different locations on rails 450 near an operating table O. The external environment sensor system 304 of the manipulator assembly 402 includes sensors 304-1 and 304-2. In some embodiments, sensor 304-1 includes an imaging device with a field of view 452-1, where sensor data (e.g., image data) from the sensor 304-1 do not include sufficient information (e.g., image of the entire or portions of manipulator assembly 404) for determining spatial relationship between manipulator assemblies 402 and 404. In an example, as shown in FIG. 4B, manipulator assembly 404 is not in the field of view 452-1.

In the example of FIG. 4B, sensor 304-2 includes an imaging device with a field of view 452-2. In the example of FIG. 4B, manipulator assembly 404 is in the field of view 452-2, but is partially or entirely occluded (e.g., by an intermediate object 453) from the sensor 304-2 such that sensor data (e.g., image data) from the sensor 304-2 do not include sufficient information (e.g., image of the entire or portions of manipulator assembly 404) for determining spatial relationship between manipulator assemblies 402 and 404. In other examples, manipulator assembly 404 is not occluded from the sensor 304-1, and sensor data (e.g., image data) from sensor 304-2 include sufficient information (e.g., image of the entire or portions of manipulator assembly 404) for determining spatial relationship between manipulator assemblies 402 and 404 by the control system.

In the example of FIG. 4B, the manipulator assembly 404 does not include an external environment sensor system 304.

In other examples, manipulator assembly 404 also includes an external environment sensor system 304.

Referring to the example of FIG. 4C, another example of the robotic system 400 with external environment sensor systems is illustrated. The robotic system 400 of FIG. 4C is substantially similar to the robotic system 400 of FIG. 4B, other than the differences described below. The external environment sensor system 304 of the manipulator assembly 404 includes sensors 304-3 and 304-4. In some embodiments, sensor 304-3 includes an imaging device with a field of view 452-3, where sensor data (e.g., image data) from the sensor 304-3 do not include sufficient information (e.g., image of the entire or portions of manipulator assembly 402) for determining spatial relationship between manipulator assemblies 402 and 404. In an example, as shown in FIG. 4C, manipulator assembly 402 is not in the field of view 452-3. In another example, manipulator assembly 402 is in the field of view 452-3, but is occluded (e.g., by a third component) from the sensor 304-3 such that sensor data (e.g., image data) from the sensor 304-3 does not include sufficient information (e.g., image of the entire or portions of manipulator assembly 402) for determining spatial relationship between manipulator assemblies 402 and 404.

In the example of FIG. 4C, sensor 304-4 includes an imaging device with a field of view 452-4, which includes the manipulator assembly 402, and sensor data (e.g., image data) from sensor 304-4 include sufficient information (e.g., image of the entire or portions of manipulator assembly 402) for determining spatial relationship between manipulator assemblies 402 and 404. In that example, manipulator assembly 402 is not occluded from the sensor 304-4.

Referring to the example of FIG. 4D, yet another example of the robotic system 400 with external environment sensor systems is illustrated. In the example of FIG. 4D, the plurality sensors of the external environment sensor system may include a reflection-based emitter-receiver sensor. For example, the external environment sensor system 304 of manipulator assembly 402 includes an emitter-receiver sensor 304-5 that may detect spatial relationships (e.g., distances, orientations) of nearby objects. The emitter-receiver sensor 304-5 may be an optical time-of-flight sensor, include an emitter 454 (e.g., configured to emit infrared light 458), and a receiver 456 (e.g., configured to receive the reflected infrared light 460) to determine the distance of an object (e.g., manipulator assembly 404).

Referring to the example of FIG. 4E, yet another example of the robotic system 400 with external environment sensor systems is illustrated. The robotic system 400 of FIG. 4E is substantially similar to the robotic system 400 of FIG. 4B, other than the differences described below. The external environment sensor system 304 of the manipulator assembly 404 includes sensors 304-1 and 304-2. Sensor 304-1 includes an imaging device with a field of view 452-1, where sensor data (e.g., image data) from the sensor 304-1 do not include sufficient information (e.g., image of the entire or portions of manipulator assembly 402) for determining spatial relationship between manipulator assemblies 402 and 404. Sensor 304-2 includes an imaging device with a field of view 452-2, where sensor data (e.g., image data) from the sensor 304-2 include partial view of manipulator assembly 402. In various embodiments, such partial-view sensor data from the sensor 304-2 may provide sufficient information for determining spatial relationship between manipulator assemblies 402 and 404, where the control system may determine the spatial relationship using both the partial-view sensor data and full kinematic information of both manipulator assemblies 402 and 404.

Referring to the examples of FIGS. 5A, 5B, 5C, 5D, and 5E, various configurations of external environment detection sensor systems in a robotic system 500 including a third component in addition to two manipulator assemblies having separately movable bases are illustrated. While in the example of FIGS. 5A-5E, the third component is another manipulator assembly on a separately movable base, in various embodiments, the third component may be any suitable components with movable or fixed bases, including e.g., posts, clamps, fixtures, etc. in the operating environment including the robotic system 500.

Referring to the example of FIG. 5A, a robotic system 500 is illustrated. The robotic system 500 is substantially similar to the robotic system 400 of FIG. 4A other than the differences described below. The robotic system 500 includes a third component in addition to two manipulator assemblies. In the example of FIG. 5A, the third component includes a manipulator assembly 502. The manipulator assembly 502 includes a base 504 that is physically separate and independent from the base 406 of the manipulator assembly 402 and the base 422 of the manipulator assembly 404. The manipulator assembly 502 includes a structural support 508 and a manipulator 510. In the example of FIG. 5A, a tool 512 is mounted on the manipulator 510, and thus the manipulator assembly 502 can be considered to further include the mounted tool 512. The tool 512 includes a shaft 514, a wrist 516 coupled to the distal end of the shaft 514, and an end effector 518 coupled to the wrist 516. The base 504 has a reference frame 506, which may also be denoted as b3. The shaft 514 of the tool 512 has a reference frame, and a transformation from the base reference frame 506 to the shaft reference frame may be determined based on the forward kinematics of the manipulator assembly 502.

In various embodiments, the relative positions and orientations of the bases 504, 406, and 422 are unknown. As discussed in detail below, in various embodiments, the transformation $^{b1}T_{b2}$ from the imaging base frame b1 418 to the tool base frame b2 434 may be determined using the third component (e.g., manipulator assembly 502). In an example, the transformation $^{b1}T_{b2}$ may be determined as follows:

$$^{b1}T_{b2} = {}^{b1}T_{b3} * {}^{b3}T_{b2}, \quad (1)$$

where $^{b1}T_{b3}$ is the transformation from imaging base frame b1 418 to base reference frame b3 506, and where $^{b3}T_{b2}$ is the transformation from base reference frame b3 506 to base reference frame b2 422. The transformation T may include a full 6×6 transformation matrices, a 3×3 rotation matrix (also referred to as R), or any suitable transformation format.

Referring to the example of FIG. 5B, an example of the robotic system 500 with external environment sensor systems is illustrated. The robotic system 500 includes manipulator assemblies 402, 404, and 502 mounted on rails near operating table O. Sensor data from sensor 304-2 of the external environment sensor system 304 of the manipulator assemblies 402 do not provide sufficient spatial information about manipulator assembly 404 (e.g., because of occlusion 520) relative to manipulator assembly 402, although manipulator assembly 404 is in the field of view of sensor 304-2 if there is no occlusion 520. Sensor data from sensor 304-7 of the external environment sensor system 304 of the manipulator assemblies 402 do not provide sufficient spatial information about manipulator assembly 404 (e.g., because of occlusion or limited field of view of an image sensor 304-7) relative to manipulator assembly 402. Sensor data from sensor 304-8 of the external environment sensor system 304 of the manipulator assembly 404 do not provide sufficient spatial information about manipulator assembly 402 (e.g., because of occlusion or limited field of view of an image sensor 304-8) relative to manipulator assembly 404.

In the example of FIG. 5B, sensor data from sensor 304-7 of the external environment sensor system 304 of the manipulator assembly 402 provide sufficient spatial information about manipulator assembly 502 relative to manipulator assembly 402. As such, the control system may determine a first alignment relationship between manipulator assemblies 402 and 502 (which is the alignment relationship between corresponding bases b1 and b3) using sensor data from sensor 304-7, e.g., by determining the transformation $^{b1}T_{b3}$.

Sensor data from sensor 304-8 of the external environment sensor system 304 of the manipulator assembly 404 provide sufficient spatial information about manipulator assembly 502 relative to manipulator assembly 404. As such, the control system may determine a second alignment relationship between manipulator assemblies 404 and 502 (which is the alignment relationship between corresponding bases b2 and b3) using sensor data from sensor 304-8, e.g., by determining the transformation $^{b3}T_{b2}$.

The control system may then determine the alignment relationship between manipulator assemblies 402 and 404 based on the first and second alignment relationships, e.g., by determining transformation $^{b1}T_{b2}$ based on $^{b1}T_{b3}$ and $^{b3}T_{b2}$ according to equation (1).

In some examples, the third component (e.g., manipulator assembly 502) may not have a corresponding external environment sensor system 304. In some examples, the third component, manipulator assembly 502 may have a corresponding external environment sensor system 304, but the corresponding sensor data are not used by the control system for determining the alignment relationship between manipulator assemblies 402 and 404.

Referring to the example of FIG. 5C, another example of the robotic system 500 with external environment sensor systems is illustrated. The robotic system 500 includes manipulator assemblies 402, 404, and 502 mounted on rails near operating table O. Sensor 304-7 of the external environment sensor system 304 of the manipulator assemblies 402 is substantially similar to sensor 304-7 of FIG. 5B, which do not provide sufficient spatial information about manipulator assembly 404 (e.g., because of occlusion or limited field of view of an image sensor 304-7) relative to manipulator assembly 402.

In the example of FIG. 5C, sensor data from sensor 304-7 of the external environment sensor system 304 of the manipulator assembly 402 provide sufficient spatial information about manipulator assembly 502 relative to manipulator assembly 402. As such, the control system may determine a first alignment relationship between manipulator assemblies 402 and 502 (which is the alignment relationship between corresponding bases b1 and b3) using sensor data from sensor 304-7, e.g., by determining the transformation $^{b1}T_{b3}$.

Sensor data from sensor 304-9 of the external environment sensor system 304 of the manipulator assembly 502 do not provide sufficient spatial information about manipulator assembly 402 (e.g., because of occlusion or limited field of view of an image sensor 304-9) relative to manipulator assembly 502. On the other hand, sensor data from sensor 304-9 of the external environment sensor system 304 of the manipulator assembly 502 provide sufficient spatial information about manipulator assembly 404 relative to manipulator assembly 502. As such, the control system may determine a second alignment relationship between manipulator assemblies 404 and 502 (which is the alignment relationship between corresponding bases b2 and b3) using sensor data from sensor 304-9, e.g., by determining the transformation $^{b3}T_{b2}$.

The control system may then determine the alignment relationship between manipulator assemblies 402 and 404 based on the first and second alignment relationships, e.g., by determining transformation $^{b1}T$ based on $^{b1}T_{b3}$ and $^{b3}T_{b2}$ according to equation (1).

In some examples, manipulator assembly 404 may not have a corresponding external environment sensor system 304. In some examples, manipulator assembly 404 may have a corresponding external environment sensor system 304, but the corresponding sensor data are not used by the control system for determining the alignment relationship between manipulator assemblies 402 and 404.

Referring to the example of FIG. 5D, yet another example of the robotic system 500 with external environment sensor systems is illustrated. In the example of FIG. 5D, sensor data from sensor 304-10 of the external environment sensor system 304 of the manipulator assembly 502 provide sufficient spatial information about manipulator assembly 402 relative to manipulator assembly 502. As such, the control system may determine a first alignment relationship between manipulator assemblies 402 and 502 (which is the alignment relationship between corresponding bases b1 and b3) using sensor data from sensor 304-10, e.g., by determining the transformation $^{b1}T_{b3}$.

In the example of FIG. 5D, sensor data from sensor 304-9 of the external environment sensor system 304 of the manipulator assembly 502 provide sufficient spatial information about manipulator assembly 404 relative to manipulator assembly 502. As such, the control system may determine a second alignment relationship between manipulator assemblies 404 and 502 (which is the alignment relationship between corresponding bases b2 and b3) using sensor data from sensor 304-9, e.g., by determining the transformation $^{b3}T_{b2}$.

The control system may then determine the alignment relationship between manipulator assemblies 402 and 404 based on the first and second alignment relationships, e.g., by determining transformation $^{b1}T_{b2}$ based on $^{b1}T_{b3}$ and $^{b3}T_{b2}$ according to equation (1).

In some examples, manipulator assemblies 402 and 404 may not have a corresponding external environment sensor system 304. In some examples, one or more of manipulator assemblies 402 and 404 have a corresponding external environment sensor system 304, but the corresponding sensor data are not used by the control system for determining the alignment relationship between manipulator assemblies 402 and 404.

Referring to the example of FIG. 5E, yet another example of the robotic system 500 with external environment sensor systems is illustrated.

Sensor data from sensor 304-10 of the external environment sensor system 304 of the manipulator assembly 502 do not provide sufficient spatial information about manipulator assembly 404 (e.g., because of occlusion or limited field of view of an image sensor 304-10) relative to manipulator assembly 502. On the other hand, sensor data from sensor 304-10 of the external environment sensor system 304 of the manipulator assembly 502 provide sufficient spatial information about manipulator assembly 402 relative to manipulator assembly 502. As such, the control system may determine a second alignment relationship between manipulator assemblies 402 and 502 (which is the alignment relationship between corresponding bases b2 and b3) using sensor data from sensor 304-10, e.g., by determining the transformation $^{b1}T_{b3}$.

In the example of FIG. 5E, sensor data from sensor 304-11 of the external environment sensor system 304 of the manipulator assembly 404 do not provide sufficient spatial information about manipulator assembly 402 (e.g., because of occlusion or limited field of view of an image sensor 304-11) relative to manipulator assembly 402. On the other hand, sensor data from sensor 304-11 provide sufficient spatial information about manipulator assembly 502 relative to manipulator assembly 404. As such, the control system may determine a first alignment relationship between manipulator assemblies 402 and 502 (which is the alignment relationship between corresponding bases b1 and b3) using sensor data from sensor 304-7, e.g., by determining the transformation $^{b1}T_{b3}$.

The control system may then determine the alignment relationship between manipulator assemblies 402 and 404 based on the first and second alignment relationships, e.g., by determining transformation $^{b1}T_{b2}$ based on $^{b1}T_{b3}$ and $^{b3}T_{b2}$ according to equation (1).

In some examples, manipulator assembly 402 may not have a corresponding external environment sensor system 304. In some examples, manipulator assembly 402 may have a corresponding external environment sensor system 304, but the corresponding sensor data are not used by the control system for determining the alignment relationship between manipulator assemblies 402 and 404.

Referring to the example of FIG. 6, a flowchart provides a method 600 for performing a registration process for manipulator assemblies that are separately movable relative each other. The method 600 begins at process 602, where an operating environment in which a robotic system operates is provided, and the robotic system includes first and second manipulator assemblies having separately movable bases. In the examples of FIGS. 4A-5E, an operating environment for a robotic system (e.g., a robotic system 400 or 500) including manipulator assemblies 402 and 404 is provided.

The method 600 may proceed to process 604, where a control system receives sensor data including first sensor data from a plurality of sensors on the first manipulator assembly to provide the operating environment external to the first manipulator assembly. In the examples of FIGS. 4A-5E, a control system receives first sensor data, if available, from a plurality of sensors of an external environment sensor system 304 disposed on the manipulator assembly 402. The first sensor data may be from sensors located on various portions (e.g., different links and/or joints) of the manipulator assembly 402. In some examples, the information for operating environment external to the first manipulator assembly provides spatial information (e.g., orientation, position, etc.) of the other manipulator assemblies (e.g., manipulator assembly 404) relative to the manipulator assembly 402.

It is noted that while in the description herein, manipulator assembly 402 is used as an example of first manipulator assembly and manipulator assembly 404 is used as an example of second manipulator assembly, in various examples, the terms "first" and "second" may be reversed such that manipulator assemblies 402 and 404 may be second and first manipulator assemblies respectively.

The method 600 may proceed to process 606, where the control system receives sensor data including second sensor data from a plurality of sensors on the second manipulator assembly to provide the operating environment external to the second manipulator assembly. In the examples of FIGS. 4A-5E, a control system receives second sensor data, if available, from a plurality of sensors of an external environment sensor system 304 disposed on the manipulator assembly 404. The second sensor data may be from sensors located on various portions (e.g., different links and/or joints) of the manipulator assembly 404. In some examples, the information for operating environment external to the second manipulator assembly provides spatial information (e.g., orientation, position, etc.) of the other manipulator assemblies (e.g., manipulator assembly 402) relative to the manipulator assembly 404.

The method 600 may proceed to process 608, where the control system determines whether the received sensor data (i.e., the received first and second sensor data) is sufficient to establish an alignment relationship (including e.g., a transformation) between the first and second manipulator assemblies.

In some embodiments, at process 608, the control system determines that the received sensor data is sufficient to establish an alignment relationship between first and second manipulator assemblies. In those embodiments, the method 600 may proceed to process 616 to perform an adjustment operation.

In some embodiments, the adjustment operation of process 616 may include a process 618, where the control system may provide an indication (e.g., on a display) for an operator to add a sensor intermediary into the operating environment. After receiving the indication, an operator may add a sensor intermediary into the operating environment. In the examples of FIGS. 5A-5E, an operator may add a third component (e.g. manipulator assembly 502 or other component) as a sensor intermediary. Additional sensor data may be provided associated with the sensor intermediary. For example, as shown in FIGS. 5B, 5C, and 5E, the additional sensor data may include sensor data provided by sensor systems 304 (e.g., sensors 304-7, 304-8, 304-11) of manipulator assemblies 402 and/or 404, and include spatial relationship information of the third component relative to the manipulator assemblies 402 and/or 404. For further example, as shown in FIGS. 5C, 5D, and 5E, the additional sensor data may include sensor data provided by sensor system 304 (e.g., sensors 304-9, 304-10) of third component, and include spatial relationship information of manipulator assemblies 402 and/or 404 relative to the third component. Those additional sensor data may be used to establish the alignment relationship between manipulator assemblies 402 and 404 in subsequent steps.

In some embodiments, the adjustment operation of process 616 may include a process 620, where the control system may provide an indication (e.g., on a display) for an operator to move one or more of the first and second manipulator assemblies. The indication may also include suggested locations (e.g., locations on rails, locations under the top of the operation table) for the first and second manipulator assemblies to eliminate occlusion and increase sufficiency of the sensor data for determining the alignment relationship. In some examples, for table mounted systems, the indication may suggest that the manipulator assembly be mounted to the operation table at an intermediate portion of the structure support 408, and the structure support 408 is extended to underneath the operation table (i.e., below the clamp attachment point). In those examples, time-of-flight or other sensors may be used to provide a non-occluded view under the operation table.

In some examples where the robotic system includes a third component, the indication may also include suggested locations for the third component (e.g., a third manipulator assembly 502 or any other suitable third component). After receiving the indication, an operator may move one or more manipulator assemblies and/or third component to new locations (e.g., the suggested locations).

In some embodiments, the adjustment operation of process 616 may include a process 622, where the control system may automatically move one or more of the manipulator assemblies and/or third component to increase a sufficiency of the sensor data.

The method 600 may then proceed to process 624, where the control system receives updated sensor data after the adjustment operation(s) are performed, and proceed to process 608 to determine whether the updated sensor data is sufficient for establishing the alignment relationship between the first and second manipulator assemblies.

In some embodiments, at process 608, the control system determines that the sensor data is sufficient to determine alignment relationship (e.g., one or both or orientation and position relationships) between first and second manipulator assemblies. In those embodiments, the method 600 may proceed to process 610 to establish the alignment relationship.

In some embodiment, process 610 may include process 611, where the control system determines relative spatial relationship between first and second manipulator assemblies using first and/or second sensor data. An alignment relationship between the first and second manipulator assemblies is determined based on the determined relative spatial relationship.

In some embodiments where the updated sensor data includes additional sensor data associated with sensor intermediary, process 610 may include process 612, where the control system determines the alignment relationship between first and second manipulator assemblies using the additional sensor data associated with the sensor intermediary. In the example of FIGS. 5A-5E, the control system determines the alignment relationship between first and second manipulator assemblies based on the additional sensor data associated with the sensor intermediary (e.g., a third component), e.g., based on equation (1).

The method 600 may then proceed to process 614, where the control system switches from a registration mode to a tool control mode (e.g., to perform an operation on a patient on the operating table during a medical procedure). When operating in the tool control mode, the control system may control the movement of the tool relative to the imaging device frame in response to movement of a master control device associated with the tool. To effectively move the tool in the imaging device frame, the control system determines an alignment relationship between the imaging device frame and the end effector reference frame using the alignment relationship between manipulator assemblies 402 and 404 (including e.g., base transformation $^{b1}T_{b2}$) determined at the registration process).

For example, the control system may compute a transformation $^{c}T_{end\ effector}$ from the imaging device frame c to the end effector reference frame as follows:

$$^{c}T_{end\ effector} = ^{c}T_{b1} * ^{b1}T_{b2} * ^{b2}T_{end\ effector}, \quad (2)$$

where $^{c}T_{b1}$ is a transformation from the imaging device frame 420 to the imaging base frame 418, $^{b2}T_{end\ effector}$ is a transformation from the tool base frame 434 to the end effector reference frame. $^{c}T_{b1}$ and $^{b2}T_{end\ effector}$ are transformations that may be determined based on the forward and inverse kinematics of the manipulator assemblies 402 and 404 respectively, and $^{b1}T_{b2}$ is already determined previously at process 610 by the registration process.

In some embodiments, at process 614, the control system may derive a master-tool transform in response to state variable signals provided by the imaging system, so that an image of the tool in a display appears substantially connected to the master control device. These state variables generally indicate the Cartesian position of the field of view of the imaging device, as supplied by the manipulator supporting the imaging device. The control system may derive the master-tool transform using the base transformation $^{b1}T_{b2}$ determined by the registration process, such that the control system may properly control movement of the tool 14 relative to the imaging device frame in response to the movement of the master control device.

In some embodiments, an operator reference frame is defined relative to the display or to the operator viewing a display. In those embodiments, the control system may determine an alignment relationship between the input device and the operator reference device, and command motion of the second manipulator assembly based on that alignment relationship between the input device and the operator reference frame in response to the change in the pose of the input device corresponding to the second manipulator assembly.

In some embodiments, the control system determines an alignment relationship between the first manipulator assembly and the third component, where the third component is another manipulator assembly. In those embodiments, a motion of the third manipulator assembly may be commanded in response to a command from the input device, such as one based on a change in a pose of an input device, based on that alignment relationship between the first and third manipulator assembly. That input device for controlling the third manipulator assembly may be different from the input device controlling the second manipulator assembly.

In various embodiments, each of the manipulator assemblies of the robotic system (e.g., first manipulator assembly, second manipulator assembly, third manipulator assembly) may comprise any number of manipulators. For example, a manipulator assembly may comprise a single manipulator as depicted in the example of FIG. 2, or multiple manipulators mounted to a common physical base as depicted in the example of FIG. 1. As specific examples, a manipulator assembly comprising a plurality of manipulators may have two, three, four, or more manipulators mounted to a common physical base. In a first example, registration is performed between manipulator assemblies, such as between manipulator assemblies where each has one manipulator, between manipulator assemblies where each has a plurality of manipulators mounted to a common base, or between manipulator assemblies where a first manipulator assembly has a single manipulator a second manipulator assembly has a plurality of manipulators mounted to a common base. In this first example, registration between manipulator assemblies may be performed in accordance with the techniques described in this disclosure, using an external environment detection sensor system or through any appropriate technique. In a second example, the registration is performed between manipulators of a same manipulator assembly, the manipulators having a common base. In this second example where the manipulators share a common physical base, registration between the manipulators can be achieved through kinematic modeling with sufficient kinematic information regarding the configuration of the manipulators (such as provided by sensors such as shape sensors, joint sensors, etc.). providing manipulator shape information or joint position information), relative registration may be achieved using the kinematic information of the two manipulators. Alternatively or in addition, registration may also be performed in accordance with the techniques described in this disclosure, using an external environment detection sensor system or through any appropriate technique; this type of registration may be used to verify the registration achieved through kinematics, to provide a backup registration technique where the primary registration technique is insufficient (for example, where one or more sensors for the primary registration technique fail, or where sensor data for the primary registration technique is too noisy).

In various embodiments, the registration process may be performed before, during, or after an operation (e.g., a medical operation). In a medical example, the registration process may be performed before the medical operation (e.g. during set-up) outside of the patient or inside the patient. In another example, the registration process may be performed during the medical operation. In yet another example, the registration process may be performed as a back-up and/or calibration-check registration method where another registration process (e.g., a registration process based on mounting locations of the manipulator assemblies) is the primary registration process. In yet another example, the registration process may be used in a robotic system having manipulators on the same base to check and confirm registration of those manipulators with their respective tools. In yet another example, guided mounting locations of the manipulator assemblies may be used to narrow search, provide initial guess, and/or provide confirmation check for the registration process.

In this disclosure, specific words chosen to describe one or more embodiments and optional elements or features are not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes include various special device positions and orientations. The combination of a body's position and orientation define the body's pose.

Similarly, geometric terms, such as "parallel" and "perpendicular" are not intended to require absolute mathematical precision, unless the context indicates otherwise. Instead, such geometric terms allow for variations due to manufacturing or equivalent functions.

In addition, the singular forms "a", "an", and "the" are intended to include the plural forms as well, unless the context indicates otherwise. And the terms "comprises," "comprising," "includes," "has," and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components. The auxiliary verb "may" likewise implies that a feature, step, operation, element, or component is optional.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

Various instruments and portions of instruments have been described in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Although some of the examples described herein refer to surgical procedures or instruments, or medical procedures and medical instruments, the techniques disclosed optionally apply to non-medical procedures and non-medical instruments. For example, the instruments, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, and training medical or non-medical personnel. Additional example applications include use for procedures on tissue removed from human or animal anatomies (without return to a human or animal anatomy) and performing procedures on human or animal cadavers. Further, these techniques can also be used for surgical and nonsurgical medical treatment or diagnosis procedures.

Further, although some of the examples presented in this disclosure discuss teleoperational robotic systems or remotely operable systems, the techniques disclosed are also applicable to computer-assisted systems that are directly and manually moved by operators, in part or in whole. A computer is a machine that follows programmed instructions to perform mathematical or logical functions on input information to produce processed output information. A computer includes a logic unit that performs the mathematical or logical functions, and memory that stores the programmed instructions, the input information, and the output information. The term "computer" and similar terms, such as "processor" or "controller" or "control system," are analogous.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A robotic system comprising:
    a first manipulator assembly comprising a first plurality of links physically coupled to a first base, the first manipulator assembly configured to support a first tool;
    a first plurality of sensors disposed on the first manipulator assembly and not on the first tool;
    a second manipulator assembly comprising a second plurality of links physically coupled to a second base, the second base separately movable relative to the first base,
    wherein the first manipulator assembly and the second manipulator assembly are in an operating environment; and
    a processing unit including one or more processors, the processing unit configured to:
        receive first data including first sensor data from the first plurality of sensors, wherein the first sensor data provide spatial information about the operating environment external to the first plurality of links,
        in response to a determination that the first data are sufficient to establish a first alignment relationship between the first manipulator assembly and the second manipulator assembly, determine a first spatial relationship of the second manipulator assembly relative to the first manipulator assembly using the first data including the first sensor data,
        establish the first alignment relationship between the first manipulator assembly and the second manipulator assembly based on the first spatial relationship, and
        command, based on the first alignment relationship, motion of the second manipulator assembly in response to a command from a first input device operable by an operator.

2. The robotic system of claim 1, wherein:
    the spatial information about the operating environment external to the first plurality of links comprises an orientation or a position of the second manipulator assembly relative to the first manipulator assembly.

3. The robotic system of claim 1, wherein:
    the first sensor data comprises one or more images detected by the first plurality of sensors; or
    wherein the first sensor data includes data based on signals transmitted between the first plurality of sensors and a second plurality of sensors disposed on the second manipulator assembly.

4. The robotic system of claim 1, wherein the second manipulator assembly is configured to support a second tool, the robotic system further comprising:
    a second plurality of sensors disposed on the second manipulator assembly and not on the second tool;
    wherein the processing unit is further configured to:
        receive second sensor data from the second plurality of sensors, wherein the second sensor data provide spatial information about the operating environment external to the second plurality of links,
    wherein the first data used to determine the first spatial relationship further includes the second sensor data.

5. The robotic system of claim 4, wherein:
    the spatial information about the operating environment external to the second plurality of links comprises an orientation or a position of the first manipulator assembly relative to the second manipulator assembly.

6. The robotic system of claim 4, further comprising:
    a third component having a movable base different from the first manipulator assembly and the second manipulator assembly;
    wherein the spatial information about the operating environment external to the first plurality of links provided by the first sensor data comprises a spatial relationship of the third component relative to the first manipulator assembly,
    wherein the second sensor data provides information about a spatial relationship of the second manipulator assembly relative to the third component, and
    the processing unit is configured to:
        determine a second alignment relationship between the first manipulator assembly and the third component based on the first sensor data,
        determine a third alignment relationship between the second manipulator assembly and the third component based on the second sensor data, and
        determine the first alignment relationship using the second and third alignment relationships.

7. The robotic system of claim 1, further comprising:
    a third component having a movable base different from the first manipulator assembly and the second manipulator assembly;
    wherein the first data further comprises third sensor data from a third plurality of sensors disposed on the third component, the third sensor data providing spatial information about the operating environment external to the third component, and
    wherein the processing unit is further configured to:
        determine the first alignment relationship further using the third sensor data.

8. The robotic system of claim 7, wherein the processing unit is configured to determine the first alignment relationship further using the third sensor data by:
    determining a second alignment relationship between the second manipulator assembly and the third component based on the third sensor data;

determining a third alignment relationship of the first manipulator assembly relative to the third component based on the first sensor data or the third sensor data; and determining the first alignment relationship using the second and third alignment relationships.

9. The robotic system of claim 7, wherein the processing unit is configured to determine the first alignment relationship further using the third sensor data by:

in response to a determination that the data without the third sensor data are insufficient to establish the first alignment relationship, determining the first alignment relationship further using the third sensor data.

10. The robotic system of claim 7, further comprising:
a second input device operable by the operator,
wherein the third component includes a third manipulator assembly, and
wherein the processing unit is further configured to:
establish a second alignment relationship between the first and third manipulator assemblies, and
command, based on the second alignment relationship, motion of the third manipulator assembly in response to a command from the second input device.

11. The robotic system of claim 1, further comprising:
a third component having a movable base different from the first manipulator assembly and the second manipulator assembly;
a second plurality of sensors disposed on the second manipulator assembly;
wherein the first data further comprises third sensor data from a third plurality of sensors disposed on the third component, the third sensor data providing spatial information about the operating environment external to the third component,
wherein the processing unit is further configured to:
receive second sensor data from the second plurality of sensors, wherein the second sensor data provide spatial information about the operating environment external to the second plurality of links,
determine a second alignment relationship between the second manipulator assembly and the third component based on the second sensor data or the third sensor data;
determine a third alignment relationship between the first manipulator assembly and the third component based on the third sensor data; and
determine the first alignment relationship using the second and third alignment relationships.

12. The robotic system of claim 1, wherein the processing unit is further configured to:
in response to a determination that the first data including the first sensor data are insufficient to establish the first alignment relationship, perform an adjustment operation.

13. The robotic system of claim 12, wherein the adjustment operation includes:
providing an indication for an operator to add a sensor intermediary into the operating environment.

14. The robotic system of claim 12, wherein the adjustment operation includes:
providing an indication for an operator to move the first manipulator assembly or the second manipulator assembly to increase a sufficiency of the data.

15. The robotic system of claim 12, wherein the processing unit is further configured to:

make the determination that the data are insufficient by determining that the first plurality of sensors are occluded from detecting the second manipulator assembly.

16. The robotic system of claim 12, wherein the adjustment operation includes:
commanding motion of the first manipulator assembly or the second manipulator assembly to increase a sufficiency of the data.

17. The robotic system of claim 1, wherein the processing unit is further configured to:
determine the first alignment relationship further based on at least one mounting location selected from the group consisting of: a first mounting location of the first manipulator assembly and a second mounting location of the second manipulator assembly.

18. The robotic system of claim 1, further comprising:
a second plurality of sensors disposed on the second manipulator assembly or a third component different from the first manipulator assembly and the second manipulator assembly,
wherein the processing unit is further configured to:
receive second sensor data from the second plurality of sensors, wherein the second sensor data provide spatial information about the operating environment external to the second plurality of links or external to the third component, and
wherein the processing unit is configured to determine the first spatial relationship of the second manipulator assembly relative to the first manipulator assembly using the first data including the first sensor data by:
using the first sensor data and not the second sensor data in response to the first sensor data being sufficient to establish the first spatial relationship, and
using the first sensor data and the second sensor data in response to the first sensor data being insufficient to establish the first spatial relationship.

19. A method of operating a robotic system comprising a first manipulator assembly in an operating environment, the first manipulator assembly configured to support a first tool, the method comprising:
receiving first data including first sensor data from a first plurality of sensors disposed on the first manipulator assembly and not the first tool in an operating environment, the first sensor data providing spatial information about the operating environment external to a first plurality of links of the first manipulator assembly;
wherein the operating environment includes a second manipulator assembly comprising a second plurality of links physically coupled to a second base, the second base separately movable relative to a first base of the first manipulator assembly;
in response to a determination that the first data are sufficient to establish a first alignment relationship between the first manipulator assembly and the second manipulator assembly, determining a first spatial relationship between t the first manipulator assembly and the second manipulator assembly using the first data including the first sensor data;
establishing the first alignment relationship between the first manipulator assembly and the second manipulator assembly based on the first spatial relationship; and
commanding, based on the first alignment relationship, motion of the second manipulator assembly in response to a command from a first input device operated by an operator.

20. The method of claim 19, further comprising:
- determining a second alignment relationship between the first manipulator assembly and a third component based on the first sensor data, wherein the third component includes a movable base different from the first manipulator assembly and the second manipulator assembly;
- determining a third alignment relationship between the second manipulator assembly and the third component based on second sensor data from a second plurality of sensors disposed on the second manipulator assembly; and
- determining the first alignment relationship using the second and third alignment relationships.

21. The method of claim 19, further comprising:
- receiving third sensor data from a third plurality of sensors disposed on a third component having a movable base different from the first manipulator assembly and the second manipulator assembly; and
- determining the first alignment relationship further using the third sensor data.

22. The method of claim 21, wherein determining the first alignment relationship further using the third sensor data comprises:
- in response to a determination that the data without the third sensor data are insufficient to establish the first alignment relationship, determining the first alignment relationship further using the third sensor data.

23. The method of claim 19, further comprising:
- in response to a determination that the first data are insufficient to establish the first alignment relationship, performing an adjustment operation.

24. The method of claim 23, wherein determining whether the first data are sufficient to establish the first alignment relationship includes:
- determining that the first data are not sufficient to establish the first alignment relationship in response to a determination that the first plurality of sensors are occluded from detecting the second manipulator assembly.

25. A non-transitory machine-readable medium comprising a plurality of machine-readable instructions which, when executed by one or more processors, are adapted to cause the one or more processors to perform a method comprising:
- receiving first data including first sensor data from a first plurality of sensors disposed on a first manipulator assembly in an operating environment, the first sensor data providing spatial information about the operating environment external to a first plurality of links of the first manipulator assembly,
  - wherein the operating environment includes a second manipulator assembly comprising a second plurality of links physically coupled to a second base, the second base separately movable relative to a first base of the first manipulator assembly;
- in response to a determination that the first data are sufficient to establish a first alignment relationship between the first manipulator assembly and the second manipulator assembly, determining a first spatial relationship between the first manipulator assembly and the second manipulator assembly using the first data including the first sensor data;
- establishing the first alignment relationship between the first manipulator assembly and the second manipulator assembly based on the first spatial relationship; and
- commanding, based on the first alignment relationship, motion of the second manipulator assembly in response to a command from a first input device operated by an operator.

26. The non-transitory machine-readable medium of claim 25, wherein the method further comprises:
- in response to a determination that the first data are insufficient to establish the first alignment relationship, performing an adjustment operation.

* * * * *